(12) United States Patent
Yamane et al.

(10) Patent No.: US 7,794,843 B2
(45) Date of Patent: *Sep. 14, 2010

(54) FLUORINE-CONTAINING ORGANOPOLYSILOXANE, A SURFACE TREATMENT COMPOSITION COMPRISING THE SAME AND AN ARTICLE TREATED WITH THE COMPOSITION

(75) Inventors: Yuji Yamane, Annaka (JP); Noriyuki Koike, Takasaki (JP); Koichi Yamaguchi, Takasaki (JP); Hirofumi Kishita, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 657 days.

This patent is subject to a terminal disclaimer.

(21) Appl. No.: 11/643,988

(22) Filed: Dec. 22, 2006

(65) Prior Publication Data

US 2007/0149746 A1    Jun. 28, 2007

(30) Foreign Application Priority Data

Dec. 26, 2005   (JP) .............................. 2005-371284
Dec. 20, 2006   (JP) .............................. 2006-343447

(51) Int. Cl.
*C08G 77/46*   (2006.01)

(52) U.S. Cl. ........................... 428/447; 528/25; 528/31; 528/32; 528/34; 528/35

(58) Field of Classification Search ................... 528/35, 528/25, 31, 34, 42
See application file for complete search history.

(56) References Cited

U.S. PATENT DOCUMENTS

| | | | |
|---|---|---|---|
| 4,765,729 A | | 8/1988 | Taniguchi |
| 5,116,928 A | | 5/1992 | Inomata et al. |
| 5,228,829 A | * | 7/1993 | Niskanen et al. .......... 415/182.1 |
| 6,552,152 B2 | * | 4/2003 | Sakano et al. ................. 528/42 |
| 6,979,710 B2 | * | 12/2005 | Osawa et al. ................ 524/588 |
| 2002/0095009 A1 | * | 7/2002 | Sato et al. .................... 524/493 |
| 2003/0139620 A1 | * | 7/2003 | Yamaguchi et al. ......... 556/445 |
| 2004/0034135 A1 | * | 2/2004 | Koike et al. ................. 524/261 |
| 2007/0197758 A1 | | 8/2007 | Yamane et al. |

FOREIGN PATENT DOCUMENTS

| | | | |
|---|---|---|---|
| JP | 58-122979 A | | 7/1983 |
| JP | 58-167597 A | | 10/1983 |
| JP | 1-74268 | * | 3/1989 |
| JP | 6-5324 B | | 1/1994 |
| JP | 09-258003 A | | 10/1997 |
| JP | 11-29585 A | | 2/1999 |
| JP | 2001-188102 A | | 7/2001 |
| JP | 2002-348370 A | | 12/2002 |
| JP | 2003-113244 A | | 4/2003 |
| JP | 2003113244 A | * | 4/2003 |
| JP | 2003-238577 A | | 8/2003 |

OTHER PUBLICATIONS

Yuji Yamane et al., U.S. Appl. No. 11/898,013, filed Sep. 7, 2007.

* cited by examiner

*Primary Examiner*—Marc S Zimmer
(74) *Attorney, Agent, or Firm*—Birch, Stewart, Kolasch & Birch, LLP

(57) ABSTRACT

An organopolysiloxane represented by the following general formula (A), (B) or(C)

$$Si_n R^1{}_{2n+2} O_{n-1} \qquad (A)$$

$$Si_n R^1{}_{2n} O_n \qquad (B)$$

$$Si_n R^1{}_{2n+2} R^2{}_k O_{n-k} \qquad (C)$$

wherein $R^1$ may be the same with or different from each other and is a hydrogen atom or a monovalent organic group, $R^2$ is an alkylene group having 2 to 6 carbon atoms, n is an integer of from 2 to 40 and k is an integer of 1 to 3, characterized in that at least two $R^1$'s are represented by the following formula (i):

$$-C_y H_{2y} - \underset{\underset{X_a}{|}}{Si} - R^3{}_{3-a} \qquad (i)$$

wherein X is a hydrolyzable group, $R^3$ is an alkyl group having 1 to 4 carbon atoms or a phenyl group, y is an integer of from 1 to 5 and a is 2 or 3; and one SiOSi bond is replaced with a bond represented by the following formula (iii):

$$SiQR_f^2 QSi \qquad (iii)$$

wherein $R_f^1$ is a monovalent group containing a perfluoroether residue, $R_f^2$ is a divalent group containing a perfluoroether residue, and Q is a divalent organic group.

27 Claims, 12 Drawing Sheets

FLUORINE-CONTAINING ORGANOPOLYSILOXANE, A SURFACE TREATMENT COMPOSITION COMPRISING THE SAME AND AN ARTICLE TREATED WITH THE COMPOSITION

This application claims benefit of Japanese Patent application No. 2005-371284 filed on Dec. 26, 2005 and Japanese Patent application No. 2006-343447 filed on Dec. 20, 2006, the contents of which are hereby incorporated by reference.

FIELD OF THE INVENTION

The present invention relates to an organopolysiloxane containing a fluorinated moiety, a surface treatment composition comprising the same and an article treated by the composition. The organopolysiloxane forms a coating layer which bonds strongly to a substrate and is resistant to scrubbing, water and oil.

BACKGROUND OF THE INVENTION

Compounds containing perfluoropolyether moieties generally have very small surface free energy to have water and oil repellency, chemical resistance, lubricity, releasing property, and antifouling property. Making use of these properties, they are widely used as, for example, treatment agents to make paper or fiber water and oil repellent, antifouling agents, lubricants for magnetic storage media, oil repellent agents for precision apparatuses, releasing agents, cosmetics, and protective films.

These properties, on the other hand, mean that such a fluorine-containing compound does not bond to other materials. Even if it can be applied to a substrate, it hardly forms a coating bonded well to the substrate.

Meanwhile, it is well known that an organic compound can be bonded to a surface of glass or cloth via a silane coupling agent. The silane coupling agent has an organic functional group and a reactive silyl group, usually an alkoxy silyl group. The alkoxy silyl groups are autocondensed in the presence of moisture to form a siloxane film. At the same time, the alkoxy silyl group chemically bonds to glass or metal surface to form a resistant film. The silane coupling agents are widely used as coating agents for various substrates.

Japanese Patent Application Laid-Open No.S58-167597 discloses a fluoroaminosilane compound represented by the following formula (8):

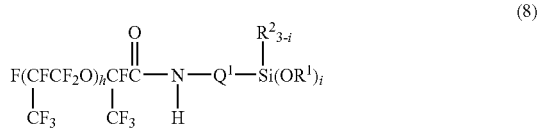

(8)

wherein $R^1$ and $R^2$ are alkyl groups having 1 to 4 carbon atoms, $Q^1$ is $CH_2CH_2CH_2$ or $CH_2CH_2NHCH_2CH_2CH_2$, h is an integer of from 1 to 4, and i is 2 or 3.

The perfluoropolyether moiety of the compound, however, is relatively short, i.e., a dimer to pentamer of hexafluoropropylene oxide, so that the aforesaid characteristics of the perfluoropolyether are not significant.

Japanese Patent Application Laid-Open No.S58-122979 discloses a water and oil repellent agent for glass surface. The agent is represented by the following formula:

(9)

wherein $Rf^1$ is a polyfluoroalkyl group having 1 to 20 carbon atoms which may contain one or more of ether group, $R^3$ is a hydrogen atom or a lower alkyl group, A is an alkylene group, $X^1$ is —$CON(R^4)$-Q- or $SO_2N(R^4)$-Q-, wherein $R^4$ is a lower alkyl group and Q is a divalent organic group, Z is a lower alkyl group, Y is a halogen atom, alkoxy group or $R^5COO$—, wherein $R^5$ is a hydrogen atom or a lower alkyl group, s is 0 or 1, t is an integer of from 1 to 3, u is an integer of from 0 to 2. The fluorinated group of this compound has carbon atoms not more than 20, so that effects of the fluorinated group are not sufficient.

Recently, needs for technology to attain foul-resistance and easy removal of fouling are increased, for example, maintenance free windows of high buildings and fingerprint-proof displays. Materials which meet these requirements are desired.

Japanese Patent Application Laid-Open No.9-258003 discloses a lens which has an antifouling layer prepared from a fluorine-containing silane compound. The fluorine-containing silane compound has both properties of aforesaid perfluoropolyether moiety and silane coupling agent. The compound has relatively larger amount of hydrolyzable groups per molecule. However, the hydrolyzable groups are present only one end of the molecule, so that bonding strength to a substrate is not large enough for the layer to be durable.

An antireflection layer, which is generally formed on visual tools and equipments, is prone to be fouled with fingerprints, sweat, saliva, or hair dressing. The fouling causes change in surface reflectance. Further, the fouling stands out as white object to be more eminent than those on an ordinary transparent object. Therefore, an antireflection layer is desired which has excellent antifouling property, and is easy to clean and durable.

Japanese Patent Publication of Examined Application No.6-5324 discloses an antireflection film having improved antifouling property. The layer is formed on an antireflective monolayer or multilayer mainly composed of silicon dioxide deposited by PVD method. The layer is composed of organopolysiloxane polymer or perfluoroalkyl group-containing polymer.

Fouling by human secretion and fingerprint, however, is difficult to wipe out from the layer and tends to extend to form a thin oily film. When it is rubbed strongly, the antireflection film itself is damaged.

Japanese Patent Application Laid-Open No.H11-29585 discloses an antireflection film having an antifouling layer prepared from a perfluoropolyether-modified aminosilane represented by the following formula (10):

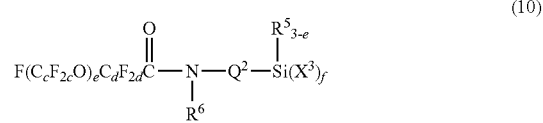

(10)

wherein $X^3$ is a hydrolyzable group, $R^5$ is a lower alkyl group, $R^6$ is a hydrogen atom or a lower alkyl group, $Q^2$ is CH$_2$CH$_2$CH$_2$ or CH$_2$CH$_2$NHCH$_2$CH$_2$CH$_2$, e is an integer of from 6 to 50, f is 2 or 3, and c and d are integers of from 1 to 3.

The aforesaid aminosilane takes a relatively long time for curing due to a relatively small wt % of the hydrolyzable group based on its molecular weight. Further, the cured coating layer does not bond strong enough to a substrate.

Japanese Patent Application Laid-Open No.2001-188102 discloses an antireflection film having an antifouling layer prepared from a perfluoropolyether moiety-containing silane coupling agent represented by the following formula (11):

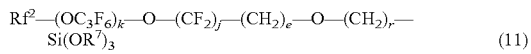

(11)

wherein Rf$^2$ is a linear or branched perfluoroalkyl group having 1 to 16 carbon atoms, R$^7$ is a C$_{1-10}$ alkyl group, k is an integer of from 1 to 50, r is an integer of from 0 to 6, j is an integer of from 0 to 3, and l is an integer of from 0 to 3, with j+l being larger than 0 and 6 or smaller.

The aforesaid perfluoropolyether moiety-containing silane coupling agent also takes a relatively long time for curing due to a relatively small wt % of the hydrolyzable group based on its molecular weight. Further, the cured coating layer does not bond strongly to a substrate.

Japanese Patent Application Laid-Open No.2002-348370 and No.2003-113244 disclose a silane coupling agent which contains a perfluoropolyether moiety and many hydrolyzable groups at one end. The silane coupling agent is described to have a good film forming property.

Japanese Patent Application Laid-Open No.2003-238577 discloses a silane coupling agent which contains a perfluoropolyether moiety represented by the following formula (12):

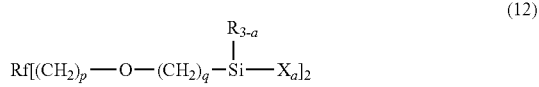

(12)

wherein Rf is a divalent linear perfluoropolyether group, R is a C$_{1-4}$ alkyl or phenyl group, X is a hydrolyzable group, p is an integer of from 0 to 2, q is an integer of from 1 to 5, and a is 2 or 3.

The above silane coupling agent has two or three hydrolyzable groups per molecule at both ends to form a coating layer which bonds strongly to a substrate. The layer is resistant to fouling and easy to clean. However, it is not resistant to scrubbing.

SUMMARY OF THE INVENTION

An object of the present invention is to provide a compound and a surface treatment composition comprising the same which forms a coating layer having excellent bonding strength to a substrate, and resistance to scrubbing, water and oil.

The present inventors have found that an organopolysiloxan having a flourine-containing moiety and hydrolyzable group introduced to an organopolysiloxane backbone forms a coating layer which is significant resistance to scrubbing, water and oil.

The present invention is an organopolysiloxane represented by the following general formula (A), (B) or (C)

(A)

(B)

(C)

wherein R$^1$ may be the same with or different from each other and is a hydrogen atom or a monovalent organic group, R$^2$ is an alkylene group having 2 to 6 carbon atoms, n is an integer of from 2 to 40 and k is an integer of 1 to 3, characterized in that at least two R$^1$'s are groups represented by the following formula (i):

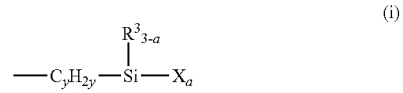

(i)

wherein X is a hydrolyzable group, R$^3$ is an alkyl group having 1 to 4 carbon atoms or a phenyl group, y is an integer of from 1 to 5 and a is 2 or 3; and one SiR$^1$ bond is represented by the following formula (ii) or one SiOSi bond is replaced with a bond represented by the following formula (iii):

(ii)

(iii)

wherein R$_f^1$ is a monovalent group containing a perfluoroether residue, R$_f^2$ is a divalent group containing a perfluoroether residue, and Q is a divalent organic group.

The present organopolysiloxane has a hydrolyzable silyl group which attains strong bonding to a substrate. It has significantly improved scrub resistance compared with the aforesaid conventional compounds which have the hydrolyzable silyl group but not an organopolysiloxane backbone. The organopolysiloxane backbone has two or more of silicon atoms which is considered to make a space between fluorine-containing moieties of neighboring molecules to attain uniform oil and water resistance. The organopolysiloxane of the present invention is useful for providing water, oil and scrub resistance to a surface of an article.

PREFERRED EMBODIMENTS OF THE INVENTION

Figure 1:
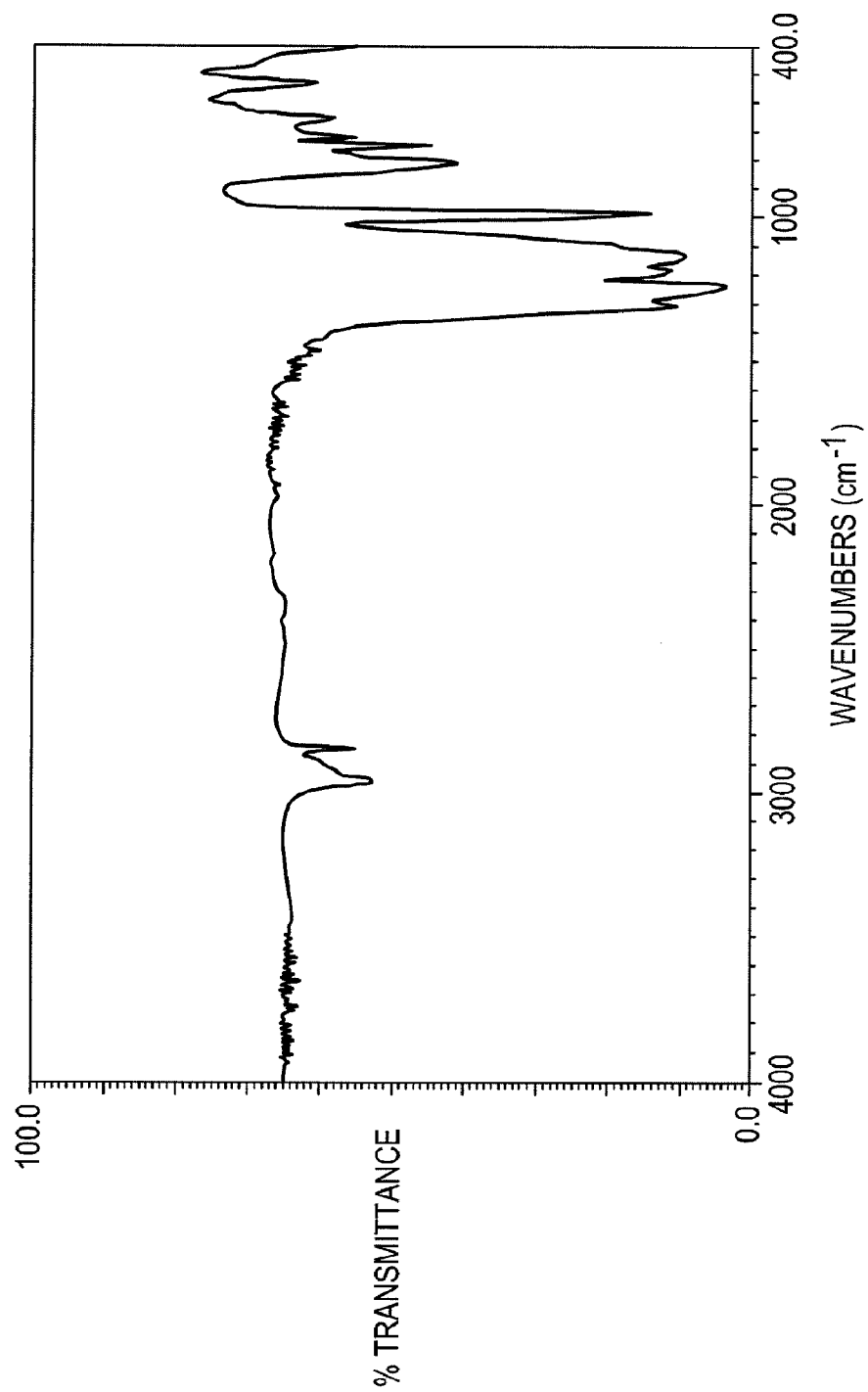
FIG. 1 is an IR chart of Compound 1.

The present organopolysiloxane has a backbone represented by the following general formula (A), (B) or (C).

(A)

(B)

(C)

The formula (A) represents a linear organopolysiloxane, the formula (B) represents a cyclic organopolysiloxane and the formula (C) represents a linear organopolysiloxane containing a Si—$R^2$—Si bond.
Examples of the organopolysiloxane represented by the formula (A), (B) or (C) are as shown below.
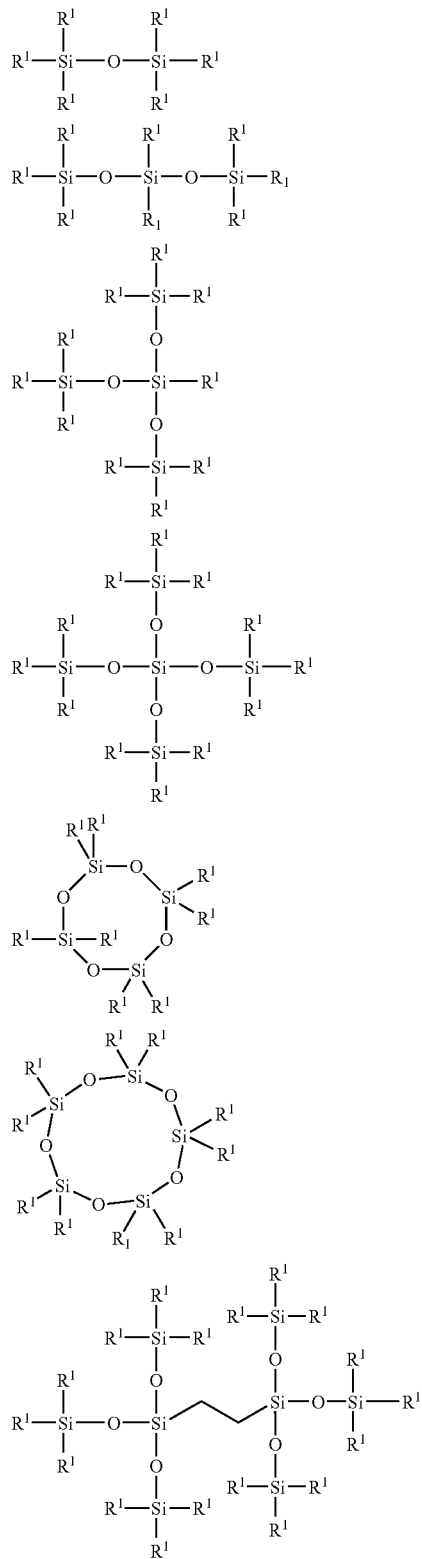

-continued

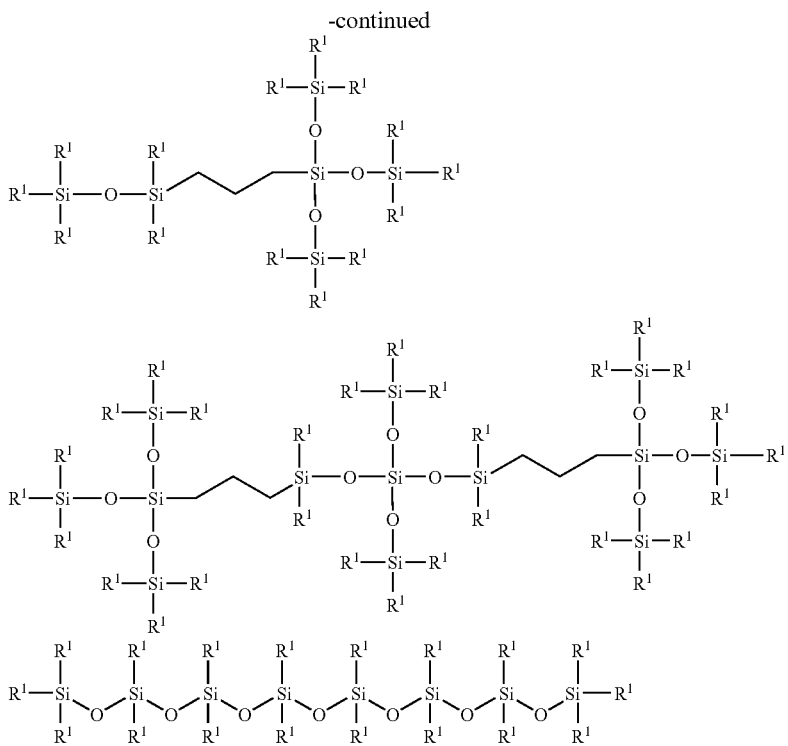

As shown above, the organopolysiloxane represented by the formula (A) or (C) may have a branch. That is, the organopolysiloxane may contain a ($R^1SiO_{3/2}$) unit where a silicon atom is bonded to three oxygen atoms, and/or a ($SiO_2$) unit where a silicon atom is bonded to four oxygen atoms.

$R^1$ may be the same with or different from each other and is a hydrogen atom or a monovalent organic group. Preferably, the organic group is an alkyl group having 1 to 8, more preferably 1 to 4, carbon atoms, or a phenyl group. $R^2$ is an alkylene group having 2 to 6 carbon atoms, preferably 2 to 4 carbon atoms, n is an integer of from 2 to 40, preferably from 2 to 10, and k is an integer of from 1 to 3.

At least two, preferably from two to six, $R^1$'s are the groups represented by the following formula (i).

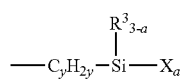 (i)

In the formula (i), X is a hydrolyzable group which may be different from each other. Examples of the hydrolyzable group include alkoxy groups having 1 to 10 carbon atoms such as methoxy, ethoxy, propoxy and buthoxy groups; oxyalkoxy groups having 2 to 10 carbon atoms such as methoxymethoxy and methoxyethoxy groups; acyloxy groups having 1 to 10 carbon atoms such as an acetoxy group; alkenyloxy groups having 2 to 10 carbon atoms such as an isopropenoxy group; halogen atoms such as chlorine, bromine, and iodine atoms. Among these, methoxy, ethoxy, iropropenoxy groups and chlorine atom are preferred.

In the formula (i), $R^3$ is a lower alkyl group having 1 to 4 carbon atoms such as methyl and ethyl groups, or a phenyl group, among which a methyl group is preferred; y is an integer of from 1 to 5, preferably 1 or 2; and a is 2 or 3, preferably 3 because of higher reactivity and stronger bonding to a substrate.

In the present organopolysiloxane backbone, a $SiR^1$ bond is the bond represented by the following formula (ii), or a SiOSi bond is replaced with the bond of the following formula (iii).

$SiQR_f^1$ (ii)

$SiQR_f^2QSi$ (iii)

$R_f^1$ is a monovalent group containing a perfluoroether residue, $R_f^2$ is a divalent group containing a perfluoroether residue, and Q is a divalent organic group.

The perfluoroether residue in $R_f^1$ or $R_f^2$ contains 1 to 500, preferably 2 to 200, more preferably 10 to 100, repeating unit represented by the general formula —$C_gF_{2g}O$—, wherein g is independently an integer of from 1 to 6, preferably from 1 to 4.

Examples of the aforesaid repeating unit —$C_gF_{2g}O$— are as follows, and two or more of them may be included in the perfluoroether residue.

—$CF_2O$—
—$CF_2CF_2O$—
—$CF_2CF_2CF_2O$—
—$CF(CF_3)CF_2O$—
—$CF_2CF_2CF_2CF_2O$—
—$CF_2CF_2CF_2CF_2CF_2CF_2O$—
—$C(CF_3)_2O$—

Preferably, $R_f^1$ comprising the above repeating units is selected from the groups represented by the following formulas (2), (3) and (4).

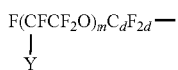 (2)

wherein m is an integer of from 2 to 200, d is an integer of from 1 to 3 and Y is F or $CF_3$;

 (3)

wherein m is an integer of from 2 to 200, and d is an integer of from 1 to 3;

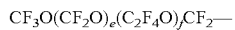 (4)

wherein each of e and f is an integer of from 0 to 200 with e+f ranging from 2 to 200, and the repeating units ($CF_2O$) and ($C_2F_4O$) may be bonded randomly.

Preferably, $R_f^2$ is selected from the groups represented by the following formulas (5), (6) and (7).

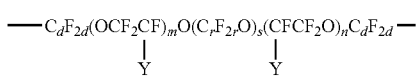 (5)

wherein Y is F or $CF_3$, which may be different with each other, and r is an integer of from 2 to 6, d is an integer of from 1 to 3, each m and n is an integer of from 0 to 200 with m+n ranging from 2 to 200, s is an integer of from 0 to 6, and the repeating units may be bonded randomly;

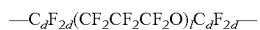 (6)

wherein l is an integer of from 1 to 200, and d is an integer of from 1 to 3;

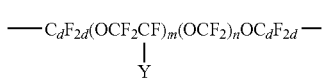 (7)

wherein Y is F or $CF_3$, d is an integer of from 1 to 3, each of m and n is an integer of from 0 to 200 with m+n ranging from 2 to 200, and the repeating units may be bonded randomly.

In the formulas (ii) and (iii), Q is a divalent group bonding $R_f^1$ or $R_f^2$ and a silicon atom of the organopolysiloxane backbone. Preferably, Q is a hydrocarbon group having 3 to 12 carbon atoms and may contain a group selected from amide, ether, ester and vinyl group. Examples of Q are as shown below, wherein the left end of each group is bonded to $R_f^1$ or $R_f^2$, and the right end to a silicon atom.

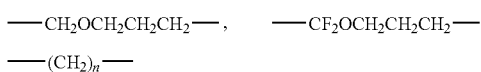

$n = 2~4$,

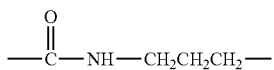

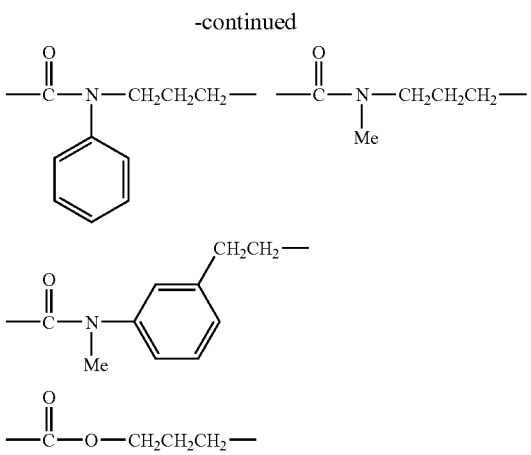

In the organopolysiloxane of the formulas (A), (B) and (C), number and location of the group of the formula (i) or bond of the formula (ii) or (iii) can be selected according to an intended properties or uses of the organosiloxane. Examples of the organosiloxane residues derived from the organopolysiloxane of the formulas (A), (B) and (C) are as shown below. Each residue shown below corresponds to the exemplary organopolysiloxane of the formulas (A), (B) or (C) shown above with $R^1$ being a methyl group.

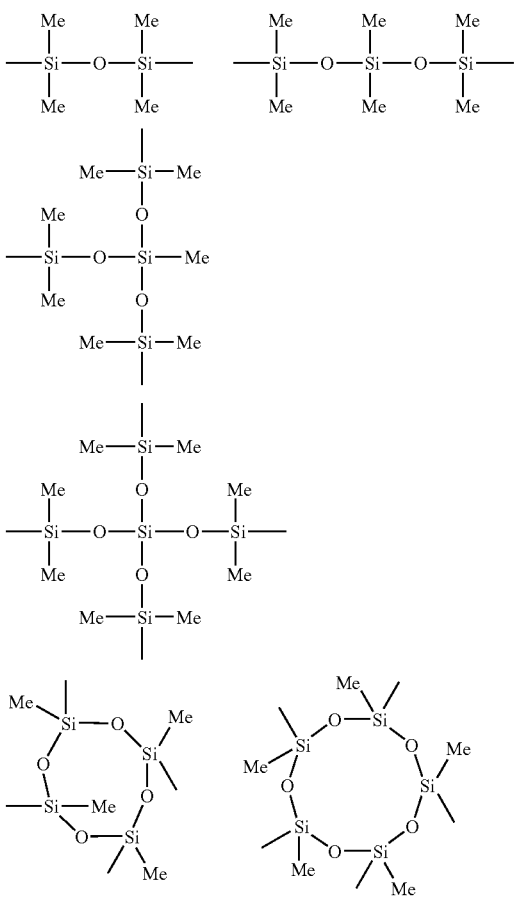

-continued

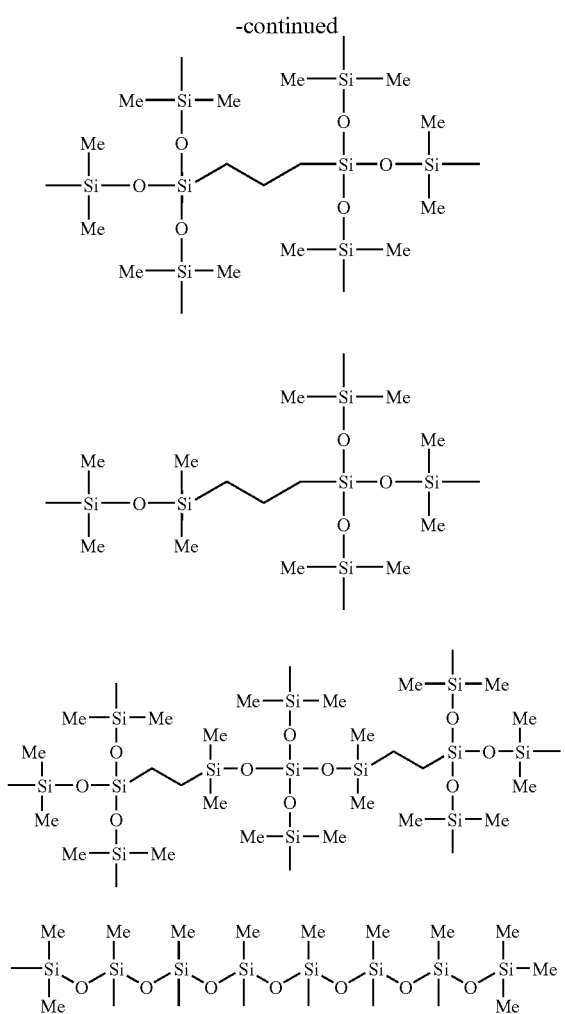

Preferably, the group of the formula (i) and the bond of the formula (ii) are located at opposite ends of the molecule. The organopolysiloxane having the bond of the formula (iii) in the middle and two groups of the formula (i) at both ends is also preferred.

The present organopolysiloxane can be prepared by the following method.

The group of the formula (i) can be introduced in an organopolysiloxane backbone by reacting a compound of the following formula (iv) having an unsaturated bond

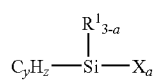

(iv)

wherein $R^1$, X, a, and y are as defined above and z is $2y-1$ or $2y$, with an organopolysiloxane having a SiH bond at a location where the group of the formula (i) is to be introduced in the presence of an addition reaction catalyst such as a platinum compound.

In a similar way, the bond of the formula (ii) can be introduced in an organopolysiloxane backbone by reacting a compound of the following formula (v) having an unsaturated bond $R_f^1 Q'$ (v)

wherein $R_f^1$ is as defined above and Q' is a group containing an unsaturated bond, with an organopolysiloxane having a SiH bond at a location where the bond of the formula (ii) is to be introduced in the presence of an addition reaction catalyst such as a platinum compound.

Examples of Q' are as shown below.

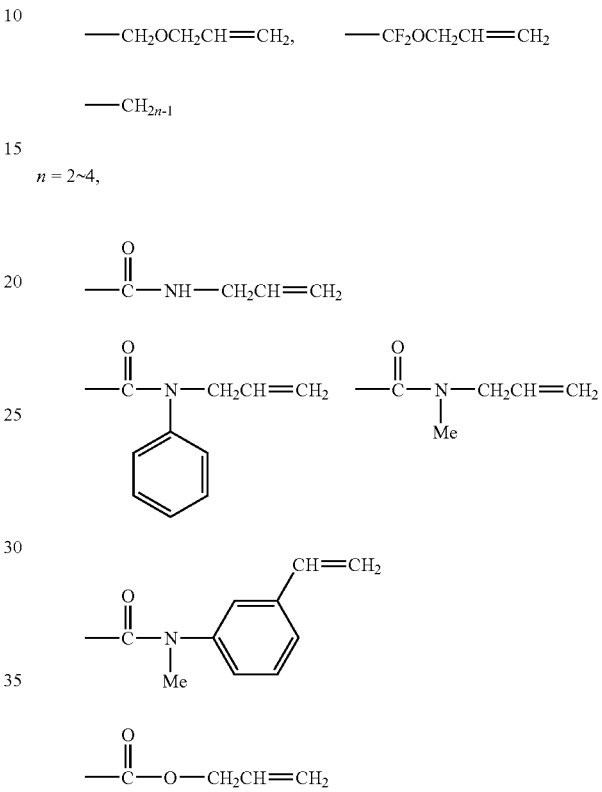

$n = 2\sim 4$,

The bond of the formula (iii) can be introduced in the organopolysiloxane backbone by reacting a compound of the following formula (vi) having unsaturated bonds at both sides of $R_f^2$ $Q' R_f^2 Q'$ (vi)

wherein $R_f^2$ and Q' are as defined above, with double equivalent amount of an organopolysiloxane having a SiH bond at a location to be reacted with an double bond of Q' in the formula (iv) in the presence of an addition reaction catalyst such as a platinum compounds.

In the above reactions, two or more types of organopolysiloxanes may be used as a mixture. The addition reaction can be performed by a conventional method.

The present invention also provides a surface treatment composition comprising the aforesaid organopolysiloxane as an active ingredient. The composition may contain partial condensation products of hydrolyzates of the organopolysiloxane which can be obtained by subjecting the organopolysiloxane to hydrolysis and condensation reactions in a conventional manner.

The surface treatment composition can contain a catalyst for hydrolysis and condensation reactions. Examples of the catalyst include organic tin compounds such as bibutyltin dimethoxide and dibutyltin dilaurate; organic titanium compounds such as tetra-n-butyl titanate; organic acids such as acetic acid and methanesulfonic acid; inorganic acids such as hydrochloric acid and sulfuric acid, among which acetic acid, tetra-n-butyl titanate, and dibutyltin dilaurate are preferred. A content of the catalyst may be a catalytic amount, which typically ranges from 0.01 to 5 parts by weight, particularly from 0.1 to 1 part by weight per 100 parts by weight of the organopolysiloxane and/or partial condensate of hydrolyzate thereof.

The surface treatment composition may contain a solvent. Examples of the solvent include fluorine-modified aliphatic hydrocarbon solvents such as perfluoroheptane and perfluoroctane; fluorine-modified aromatic hydrocarbon solvents such as m-xylenehexafluoride and bezotrifluoride; fluorine-modified ether solvents such as methyl perfluorobutyl ether, ethyl perfluorobutyl ether, and perfluoro(2-butyltetrahydrofuran); fluorine-modified alkylamine solvents such as perfluorotributylamine, and perfluorotripentylamine; hydrocarbon solvents such as petroleum benzene, mineral spirits, toluene, and xylene; ketone solvents such as acetone, methylethylketone, and methylisobutylketone. Among these, fluorinated solvents are preferred such as m-xylenehexafluoride, perfluoro(2-butyltetrahydrofuran), perfluorotributylamine and ethyl perfluorobutyl ether.

A mixture of two or more of the aforesaid solvents may be used. Preferably, the organopolysiloxane of the present invention is dissolved homogeneously. The organopolysiloxane and/or partial condensate of hydrolyzate thereof is diluted with the solvent to a concentration of from 0.01 to 50 wt %, particularly from 0.05 to 20 wt %.

The surface treatment composition may be applied to a substrate by any known methods such as brushing, dipping, spraying and vapor deposition. Applied composition is processed at a temperature selected depending on the application method. When applied by brushing or dipping, the composition is processed at a temperature preferably of from room temperature to 120° C., more preferably in a humidified environment to promote curing reaction. A cured layer of the composition typically has a thickness of from 0.1 nm to 5 µm, particularly from 1 to 100 nm.

The present surface treatment composition may be applied to paper, cloth, metal and metal oxide, glass, plastic, or ceramics to provide water and oil repellency, releasing property, or foul resistance.

The present surface treatment composition can be used for various applications, for example, fingerprint- or sebum-proof coating of optical parts such as spectacle lenses, and antireflection filter; water repellent or antifouling coating of sanitary products such as bathtubs and wash-basins; antifouling coating of window glasses of automobiles, trains, airplanes, and headlamp covers; water repellent or antifouling coating of exterior wall materials; oil-repellent coating of kitchen architectural material; fingerprint-proof coating of compact disks or DVD. It may be used also as a coating additive, a resin improver, a dispersion or flow improver for inorganic filler, and a lubricity improver for tape or film.

EXAMPLES

The present invention is explained with reference to the following examples, but not limited thereto.

Example 1

In a reactor, 50 g of perfluoropolyether compound represented by the following formula (I) having α-unsaturated bond at one end,

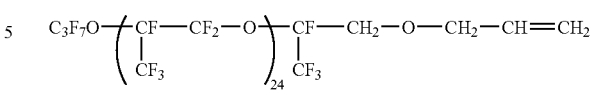

(I)

70.3 g of m-xylenehexafluoride, and 0.0442 g, i.e., 1.1×10$^{-7}$ mole as Pt, of a solution of a complex of chloroplatinic acid with a vinylsiloxane in toluene are placed and heated to 90° C. while stirring. To the mixture obtained, 21.93 g of the organopolysiloxane of the following formula (H4Q)

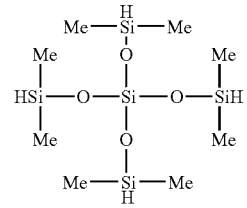

was added dropwise and heated at 90° C. for 3 hours. After confirming that no allyl group remained by $^1$H-NMR, the solvent and unreacted H4Q were removed by vacuum evaporation. The evaporation residue was treated with active carbon and 77.5 g of colorless and transparent liquid perfluoropolyether-modified organopolysiloxane were obtained.

Subsequently, in a reactor, 25 of the aforesaid perfluoropolyether-modified organopolysiloxane, 30 g of m-xylenehexafluoride, and 0.0225 g, i.e., 2.2×10$^{-6}$ mole as Pt, of a solution of a complex of chloroplatinic acid with a vinylsiloxane in toluene were placed and heated at 90° C. while stirring. To the mixture obtained, 4.63 g of vinyltrimethoxysilane was added dropwise and heated at 80° C. for 3 hours while stirring. By removing the solvent by vacuum evaporation, 26.8 g of a compound, hereinafter referred to as Compound 1, was obtained. Compound 1 was colorless and transparent liquid having a specific density of 1.55 and a refractive index of 1.336.

Figure 2:
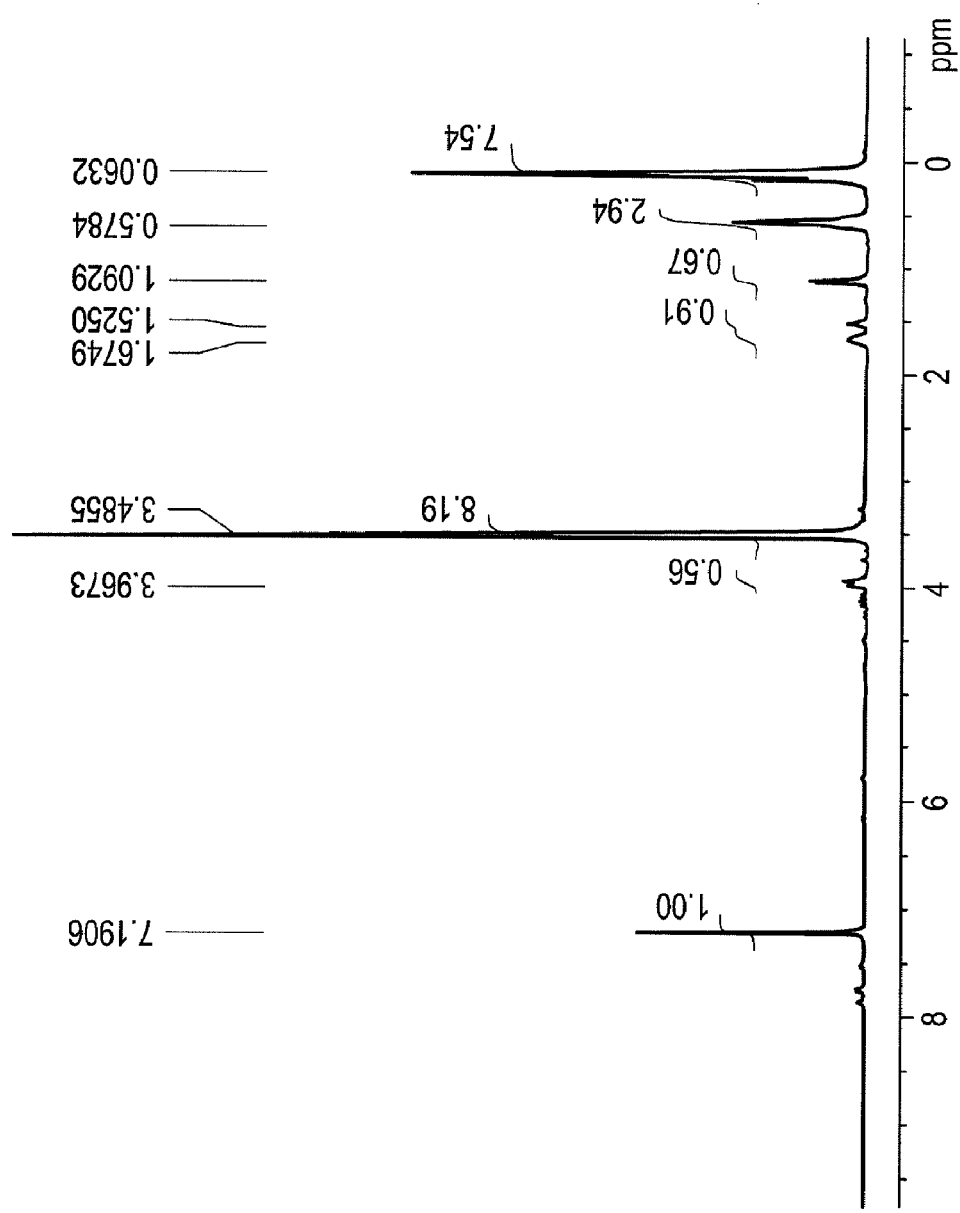
FIG. 2 is a $^1$H-NMR chart of Compound 1.

Compound 1 showed IR and $^1$H-NMR spectra as shown in FIGS. 1 and 2 with the following chemical shifts from TMS.

$^1$H-NMR spectra (δ, ppm)

| | |
|---|---|
| —SiCH$_3$, —CH— | 0.06~0.08 ppm |
| ≡SiCH$_2$CH$_2$Si≡ | 0.58 ppm |
| —CH— (CH$_3$) | 1.09 ppm |
| —CH$_2$CH$_2$Si≡ | 1.67 ppm |
| —SiOCH$_3$ | 3.49 ppm |
| —CH$_2$OCH$_2$— | 3.97 ppm |

From the above data, Compound 1 was found to have the following structure.

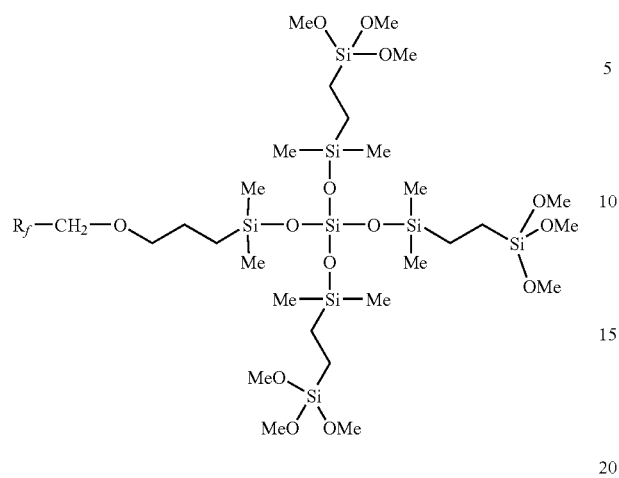

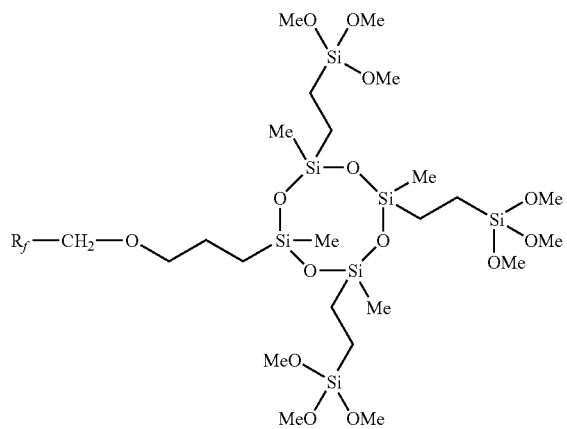

Example 3

The method used in Example 1 was repeated except that 37.3 g of organopolysiloxane of the formula shown below having a silethylene group was used in place of H4Q, and a compound, hereinafter referred to as Compound 3, was obtained. Compound 3 has a specific density of 1.71 and a refractive index of 1.330.

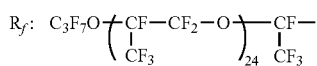

Example 2

The method used in Example 1 was repeated except that 14.5 g of tetramethylcyclotetrasiloxane, which is a cyclic siloxane called H4 was used in place of H4Q and a compound, hereinafter referred to as Compound 2, was obtained. Compound 2 has a specific density of 1.55 and a refractive index of 1.343.

Figure 3:
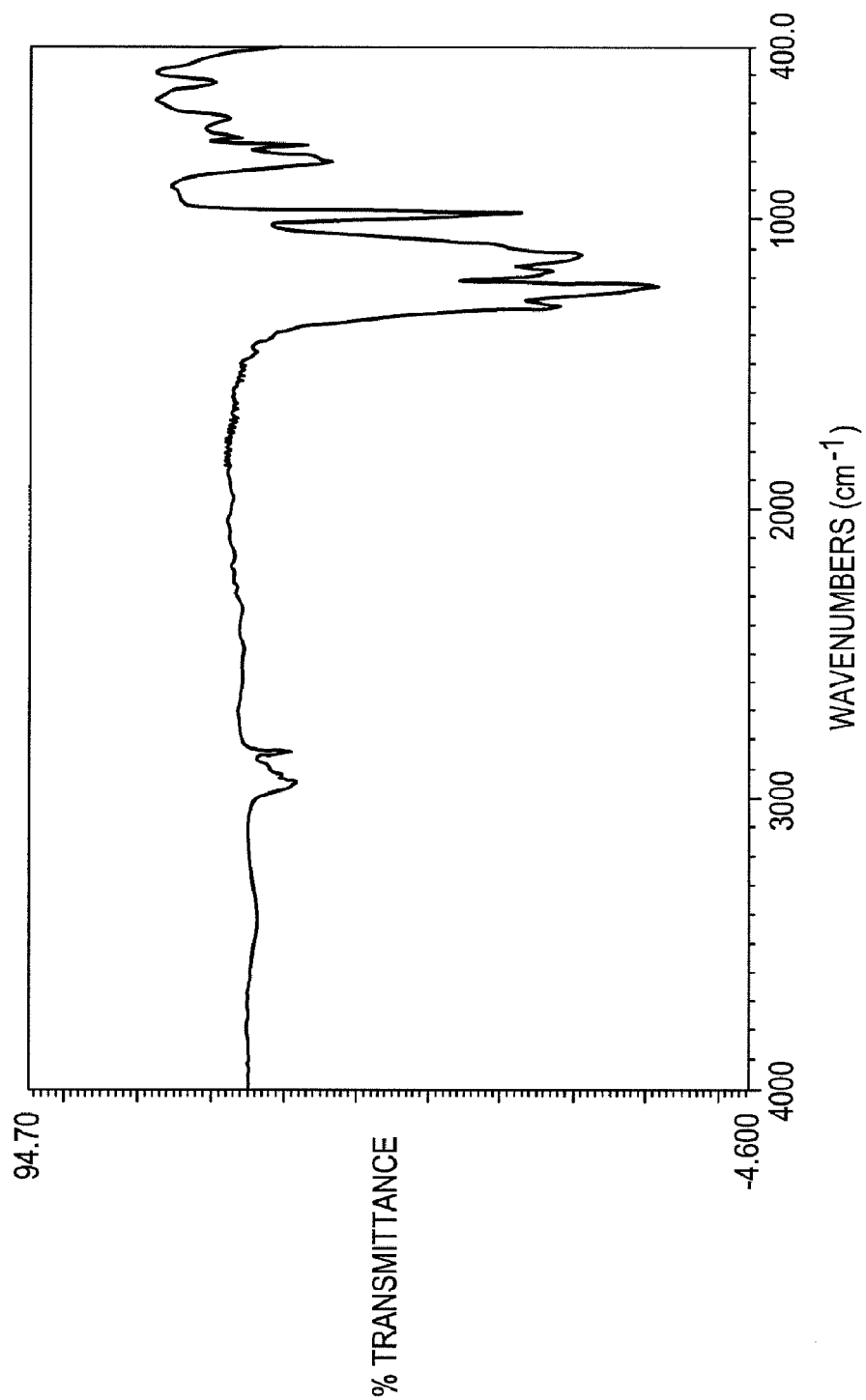
FIG. 3 is an IR chart of Compound 2.
Figure 4:
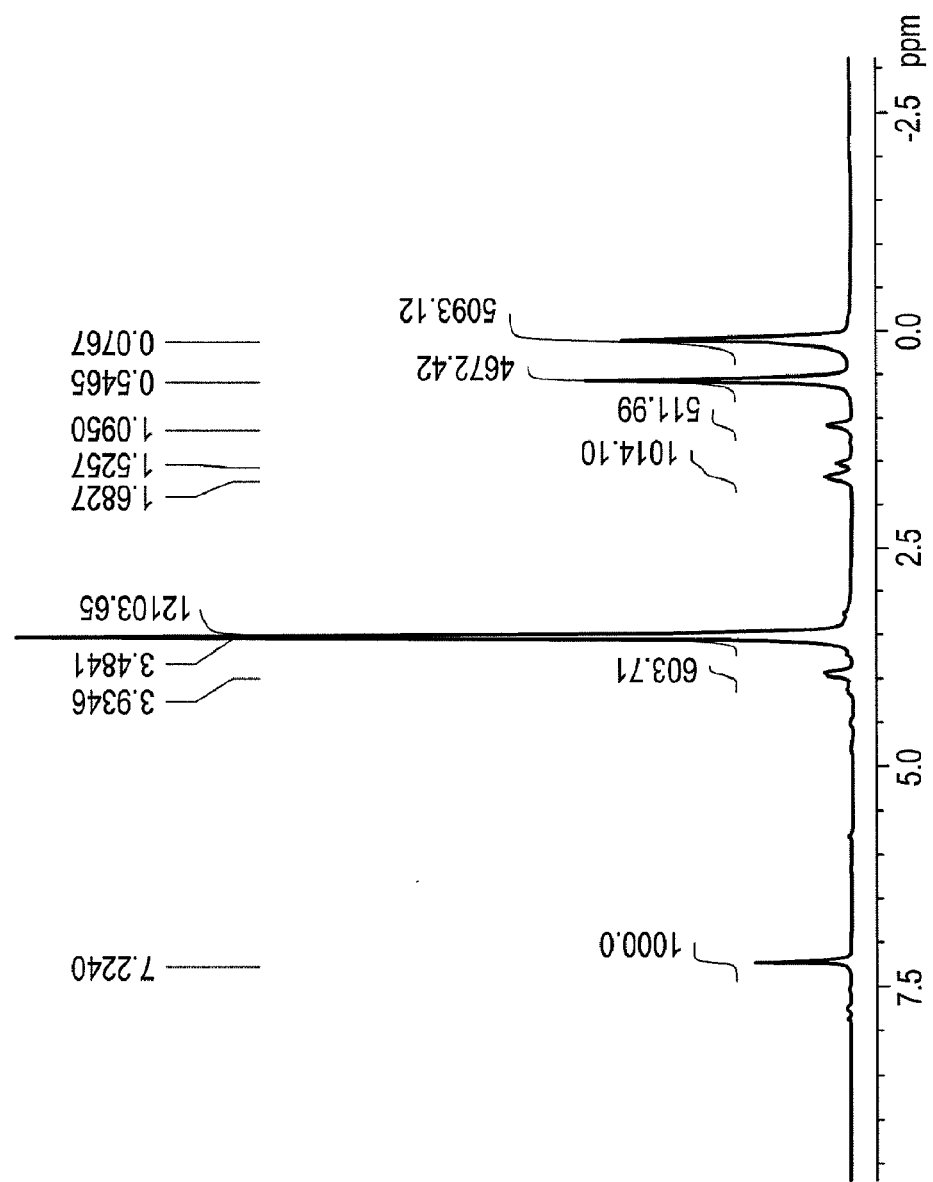
FIG. 4 is a $^1$H-NMR chart of Compound 2.

Compound 2 showed IR and $^1$H-NMR spectra as shown in FIGS. 3 and 4 with the following chemical shifts from TMS.
$^1$H-NMR spectra (δ, ppm)

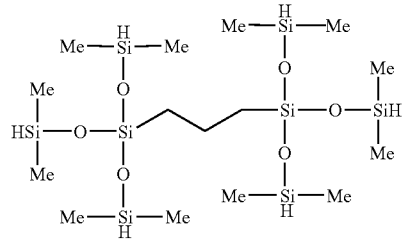

Figure 5:
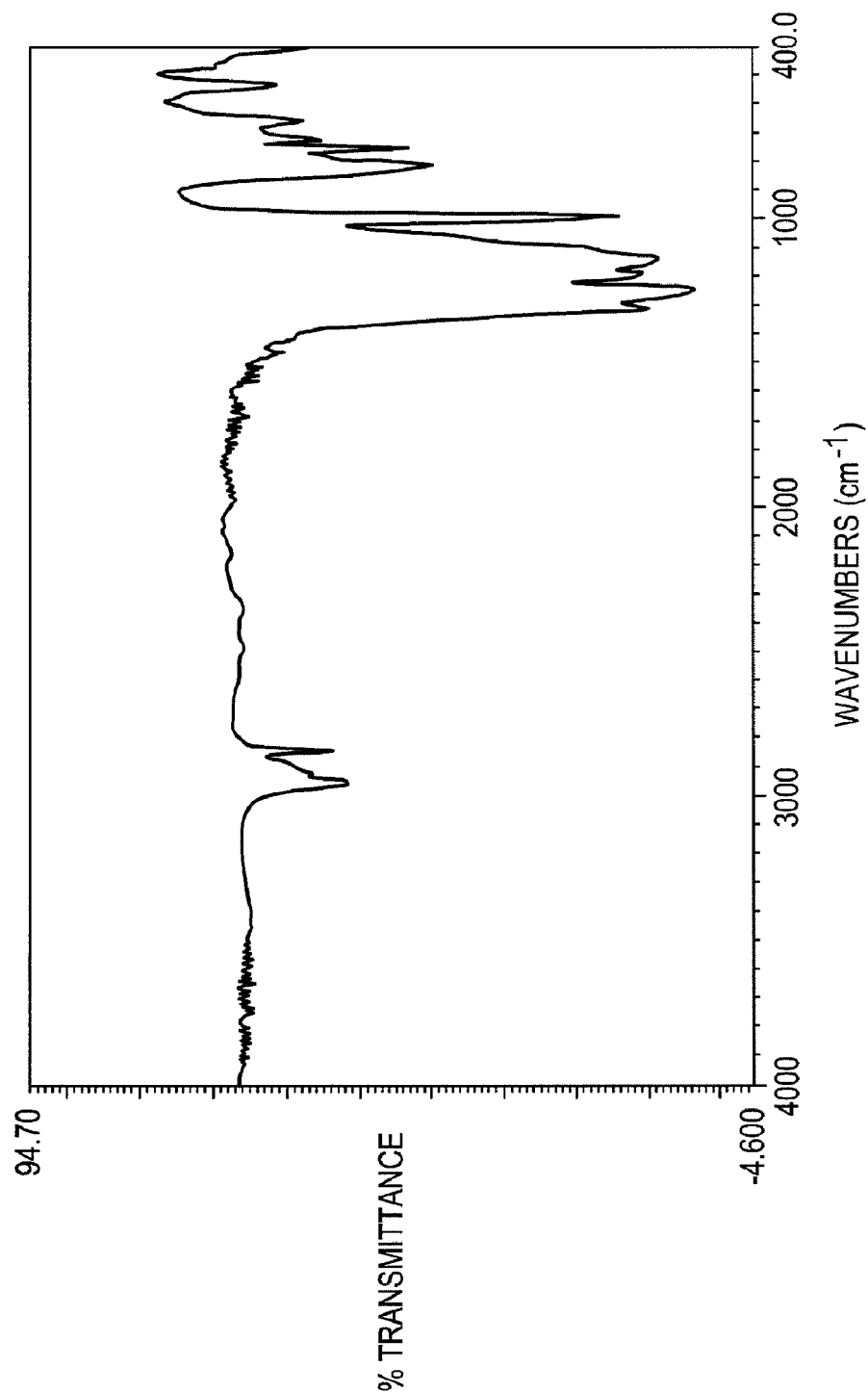
FIG. 5 is an IR chart of Compound 3.
Figure 6:
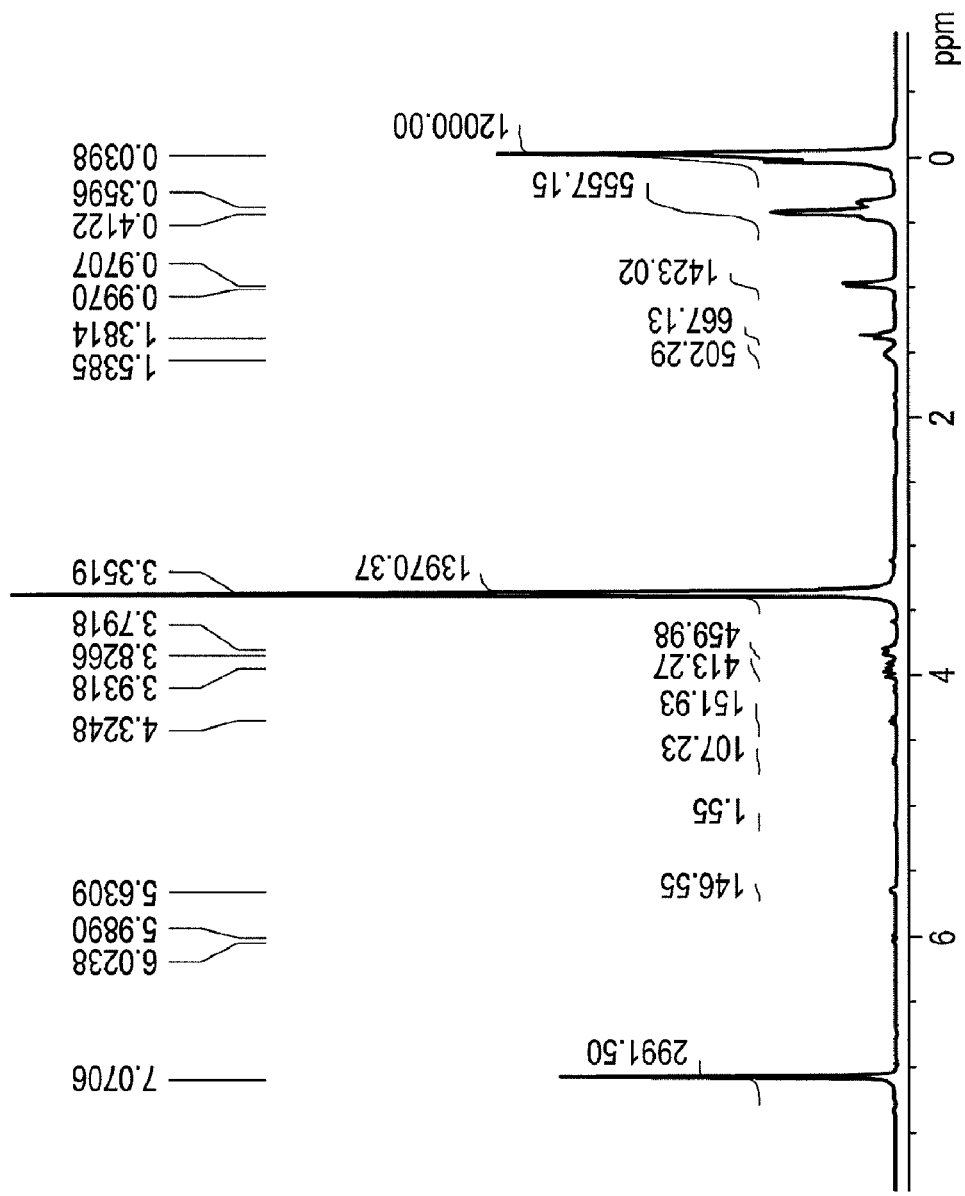
FIG. 6 is a $^1$H-NMR chart of Compound 3.

Compound 3 showed IR and $^1$H-NMR spectra as shown in FIGS. 5 and 6 with the following chemical shifts from TMS.
$^1$H-NMR spectra (δ, ppm)

| | |
|---|---|
| —SiCH$_3$, —CH— | 0.08 ppm |
| ≡SiCH$_2$CH$_2$Si≡ | 0.55 ppm |
| —CH—<br>\|<br>CH$_3$ | 1.10 ppm |
| —CH$_2$CH$_2$Si≡ | 1.68 ppm |
| —SiOCH$_3$ | 3.48 ppm |
| —CH$_2$OCH$_2$— | 3.93 ppm |

From the above data, Compound 2 was found to have the following structure.

| | |
|---|---|
| —SiCH$_3$, —CH— | −0.04 ppm |
| ≡SiCH$_2$CH$_2$Si≡ | 0.36~0.41 ppm |
| —CH—<br>\|<br>CH$_3$ | 0.97~0.41 ppm |
| —CH$_2$CH$_2$Si≡ | 1.54 ppm |
| —SiOCH$_3$ | 3.35 ppm |
| —CH$_2$OCH$_2$— | 3.79~3.82 ppm |

From the above data, Compound 3 was found to have the following structure.

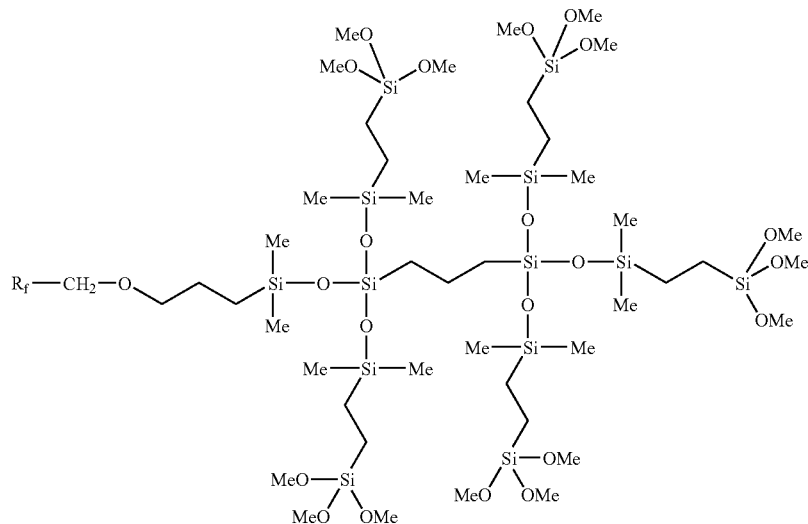

Example 4

In a reactor, 50 g of perfluoropolyether compound represented by the following formula (II) having α-unsaturated bonds at both ends,

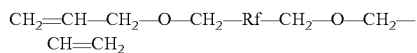

Rf: —CF$_2$(OC$_2$F$_4$)$_p$(OCF$_2$)$_q$OCF$_2$—     (II)

wherein p/q is 0.9 with p+q being about 45 on average, 70 g of m-xylenehexafluoride, and 0.0442 g, i.e., 1.1×10$^{-6}$ mole as Pt, of a solution of a complex of chloroplatinic acid with a vinylsiloxane in toluene are placed and heated to 90° C. while stirring. To the mixture obtained, 49.3 g of the organopolysiloxane of the following formula (H4Q)

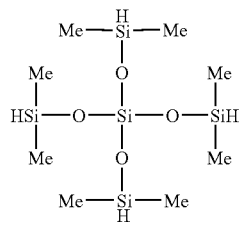

was added dropwise and heated at 90° C. for 3 hours. After confirming that no allyl group remained with $^1$H-NMR spectrum, the solvent and unreacted H4Q were removed by vacuum evaporation. The evaporation residue was treated with active carbon and 46.4 g of colorless and transparent liquid perfluoropolyether-modified organopolysiloxane were obtained.

Subsequently, in a reactor, 30 of the aforesaid perfluoropolyether-modified organopolysiloxane, 30 g of m-xylenehexafluoride, and 0.0223 g, i.e., 5.6×10$^{-8}$ mole as Pt, of a solution of a complex of chloroplatinic acid with a vinylsiloxane in toluene were placed and heated at 90° C. while stirring. To the mixture obtained, 5.76 g of vinyltrimethoxysilane was added dropwise and heated at 80° C. for 3 hours while stirring. By removing the solvent by vacuum evaporation, 33.7 g of a compound, hereinafter referred to as Compound 4, was obtained. Compound 4 has a specific density of 1.71 and a refractive index of 1.327.

Figure 7:
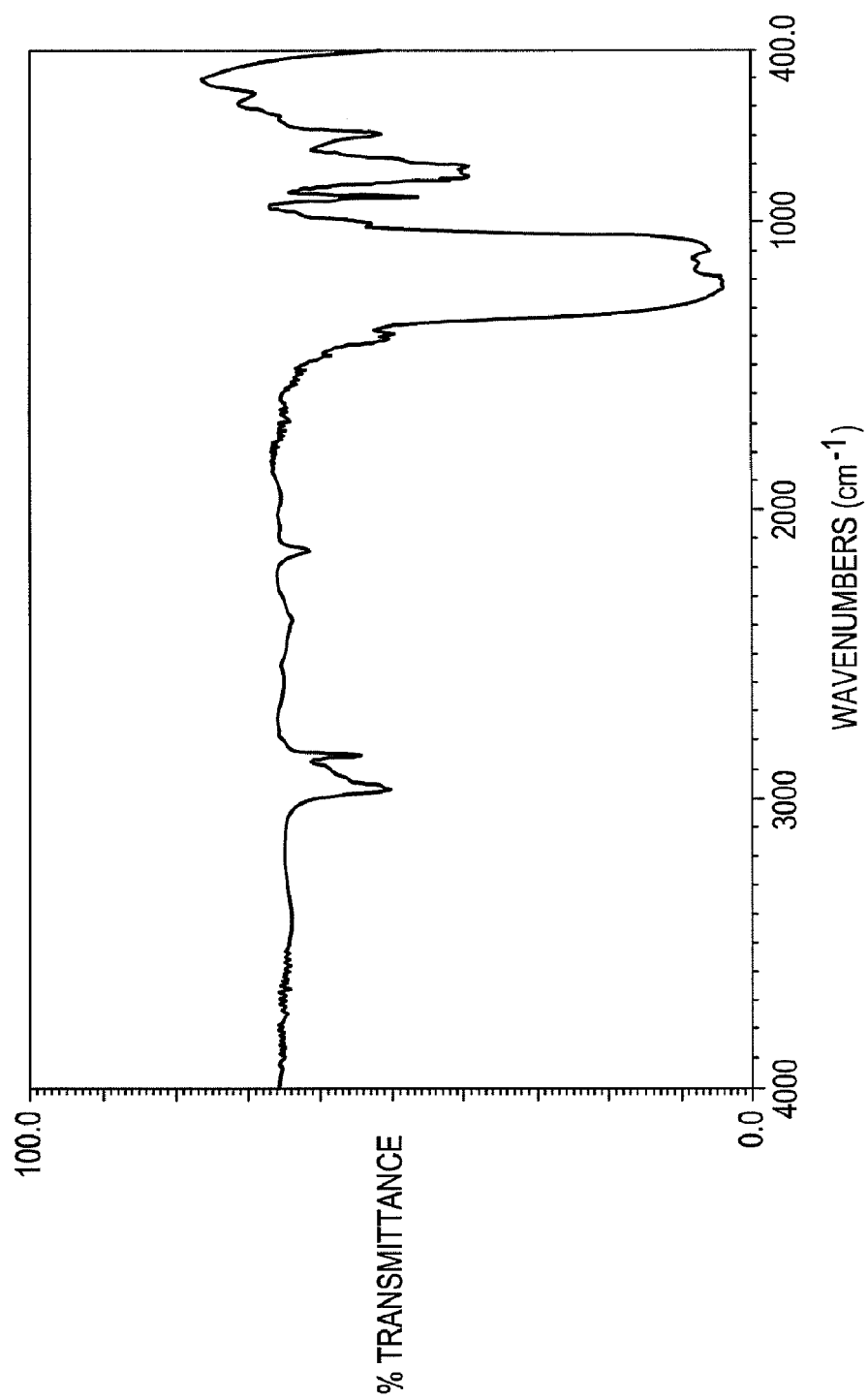
FIG. 7 is an IR chart of Compound 4.
Figure 8:
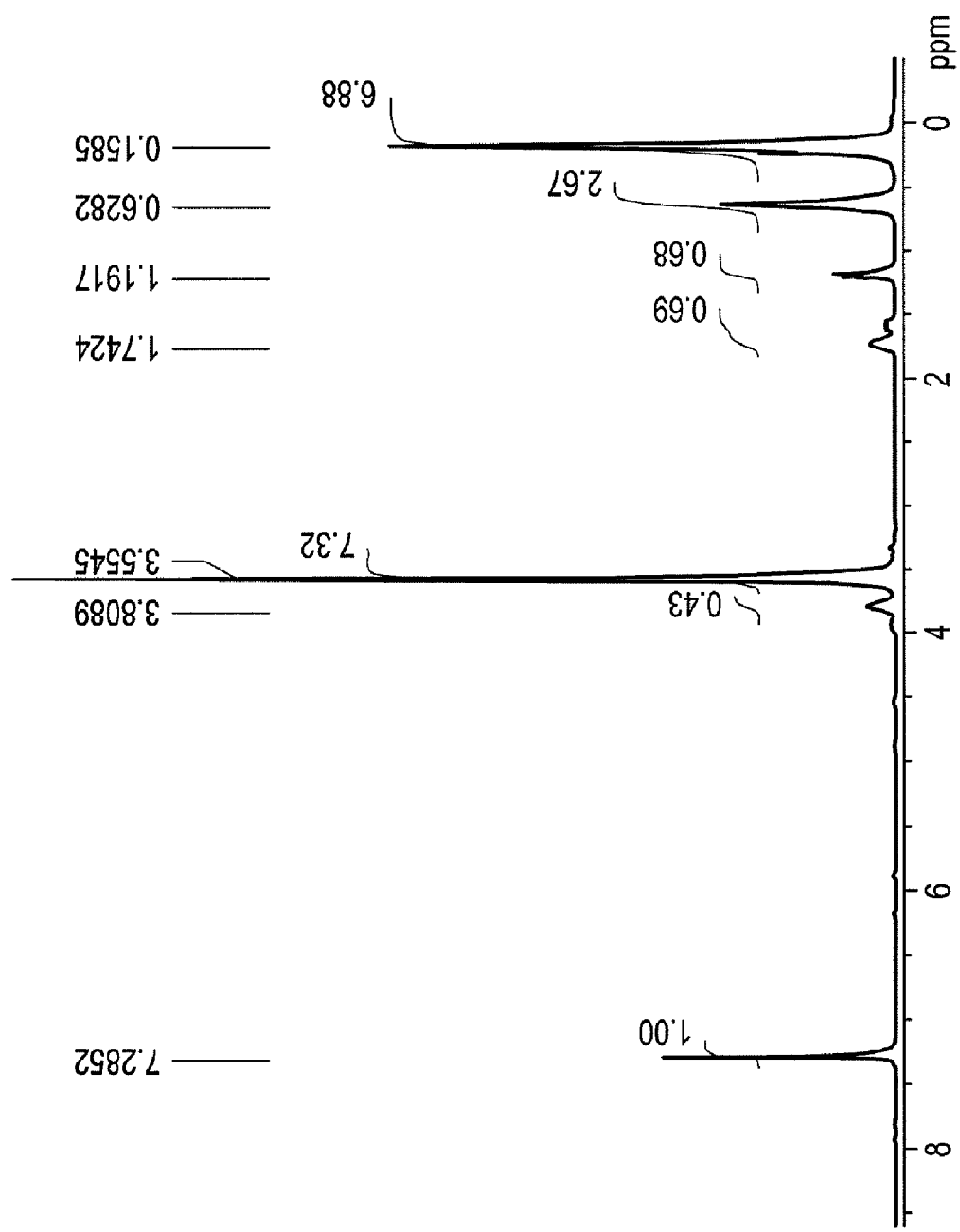
FIG. 8 is a $^1$H-NMR chart of Compound 4.

Compound 4 showed IR and $^1$H-NMR spectra as shown in FIGS. 7 and 8 with the following chemical shifts from TMS.

$^1$H-NMR spectra (δ, ppm)

| | |
|---|---|
| —SiCH$_3$, —CH— | 0.16 ppm |
| ≡SiCH$_2$CH$_2$Si≡ | 0.63 ppm |
| —CH—<br>    \|<br>   CH$_3$ | 1.19 ppm |
| —CH$_2$CH$_2$Si≡ | 1.74 ppm |
| —SiOCH$_3$ | 3.55 ppm |
| —CH$_2$OCH$_2$— | 3.80 ppm |

From the above data, Compound 4 was found to have the following structure.

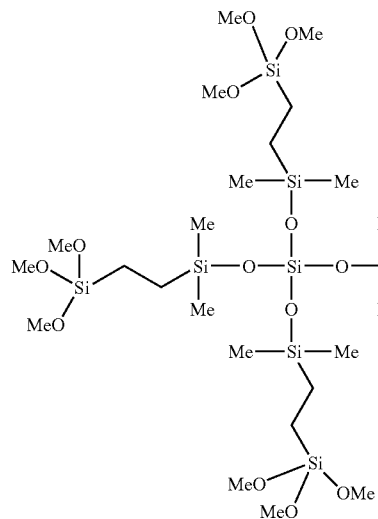
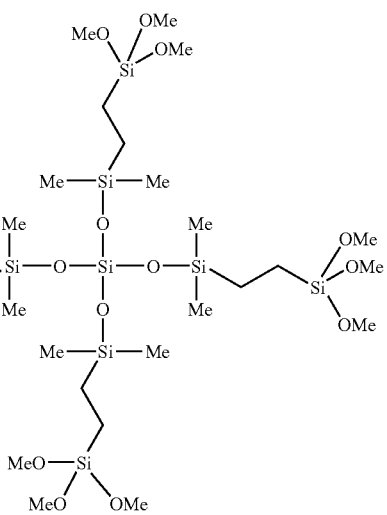

$R_f$: —$CF_2(OC_2F_4)_p(OCF_2)_qOCF_2$—

(p/q=0.9, Mw: from 4000 to 6000)

Example 5

The method used in Example 2 was repeated except that 30.4 g of the perfluoropolyether (II) as used in Example 4 was used in place of the perfluoropolyether (I) and a compound, hereinafter referred to as Compound 5, was obtained. Compound 5 has a specific density of 1.72 and a refractive index of 1.330.

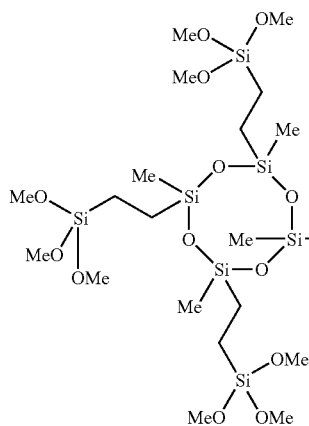

Figure 9:
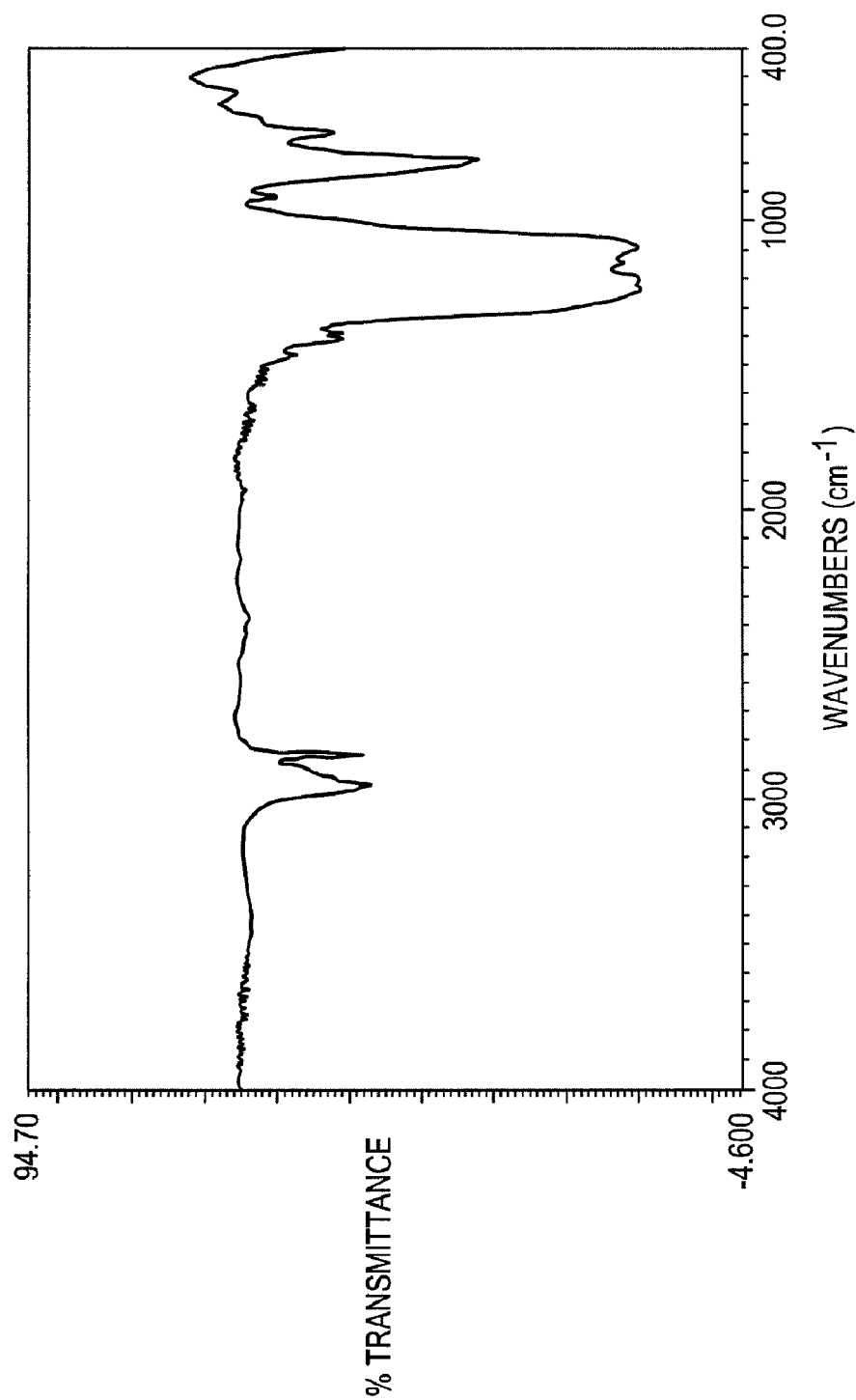
FIG. 9 is an IR chart of Compound 5.
Figure 10:
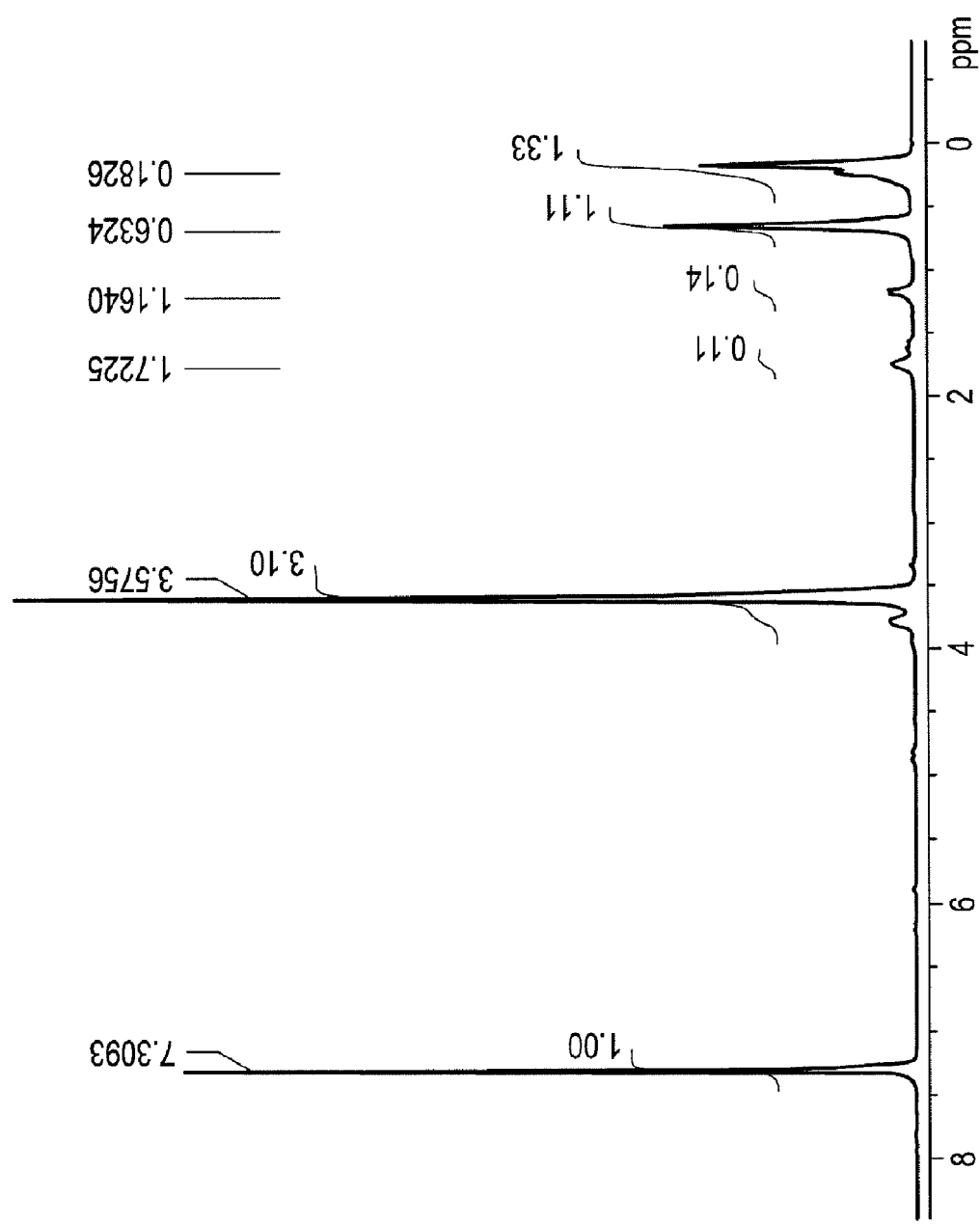
FIG. 10 is a $^1$H-NMR chart of Compound 5.

Compound 5 showed IR and $^1$H-NMR spectra as shown in FIGS. 9 and 10 with the following chemical shifts from TMS.

$^1$H-NMR spectra (δ, ppm)

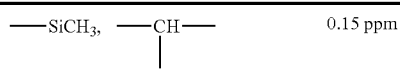

| | |
|---|---|
| -continued | |
| ≡SiCH$_2$CH$_2$Si≡ | 0.63 ppm |
| —CH—<br>\|<br>CH$_3$ | 1.15 ppm |
| —CH$_2$CH$_2$Si≡ | 1.73 ppm |
| —SiOCH$_3$ | 3.52 ppm |
| —CH$_2$OCH$_2$— | 3.78 ppm |

From the above data, Compound 5 was found to have the following structure.

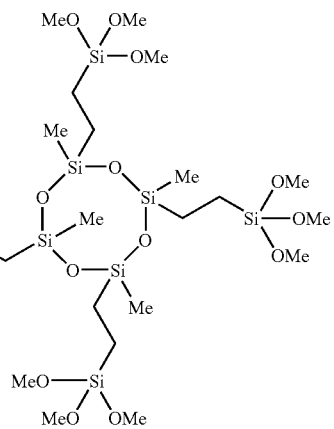

Example 6

In a reactor, 50 g of the aforesaid perfluoropolyether (II), 75 g of m-xylenehexafluoride, and 0.0442 g, i.e., 1.1×10$^{-7}$ mole as Pt, of a solution of a complex of chloroplatinic acid with a vinylsiloxane in toluene are placed and heated to 90° C. while stirring. To the mixture obtained, 8.4 g of 1:1 adduct (HM-VMS) of the tetramethyldisiloxane (HM) represented by the following formula (III) with vinyltrimethoxysilane (VMS) was added dropwise and heated at 90° C. for 2 hours.

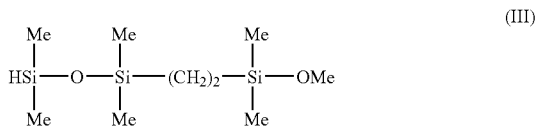

(III)

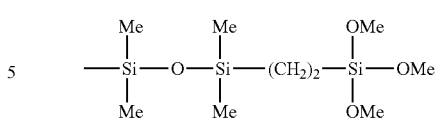

After confirming that no allyl group remained by $^1$H-NMR, the solvent and unreacted HM-VMS were removed by vacuum evaporation, and 56.3 g of a compound, hereinafter referred to as Compound 6, was obtained. Compound 6 was liquid having a specific density of 1.63 and a refractive index of 1.319.

Figure 11:
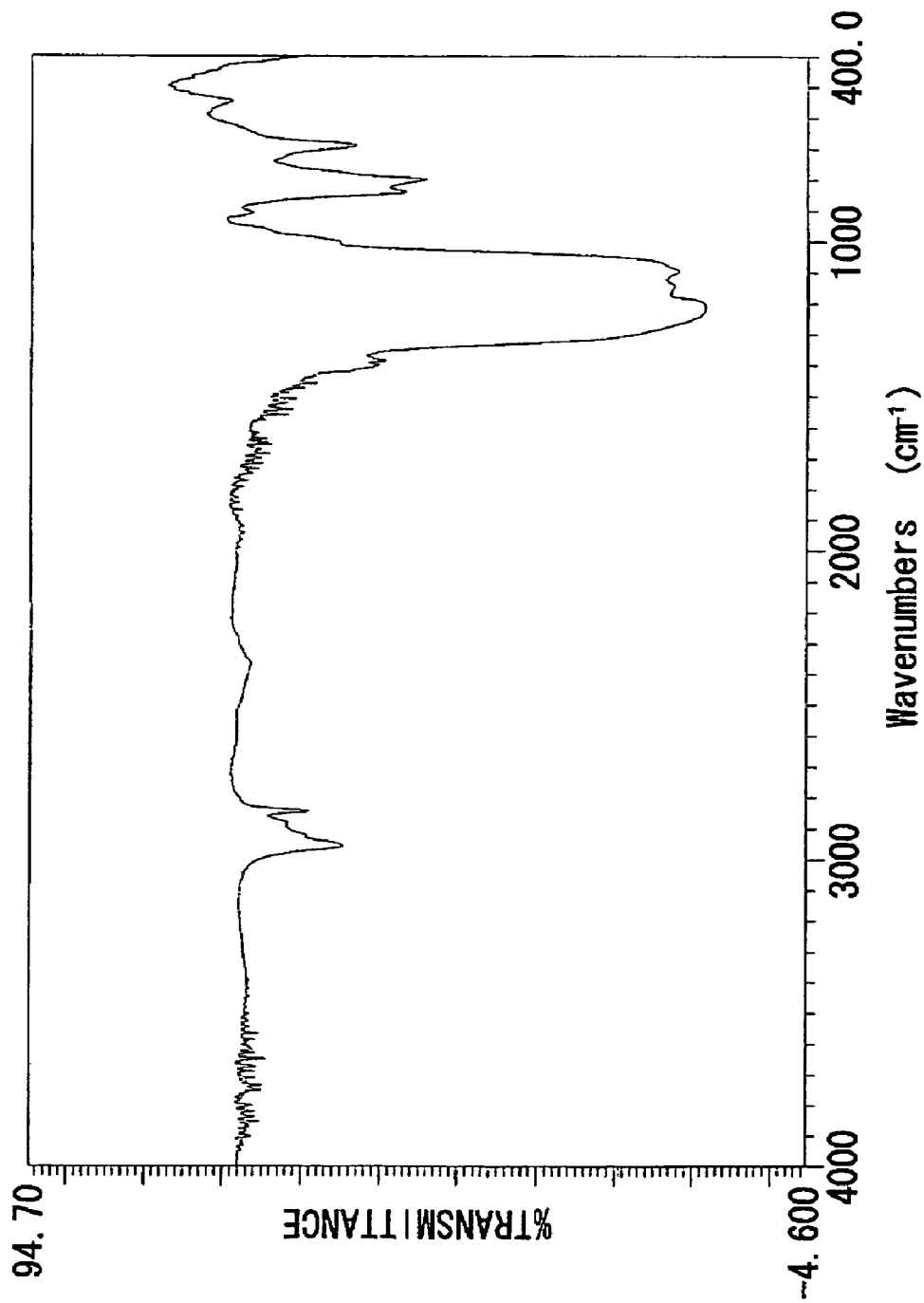
FIG. 11 is an IR chart of Compound 6.
Figure 12:
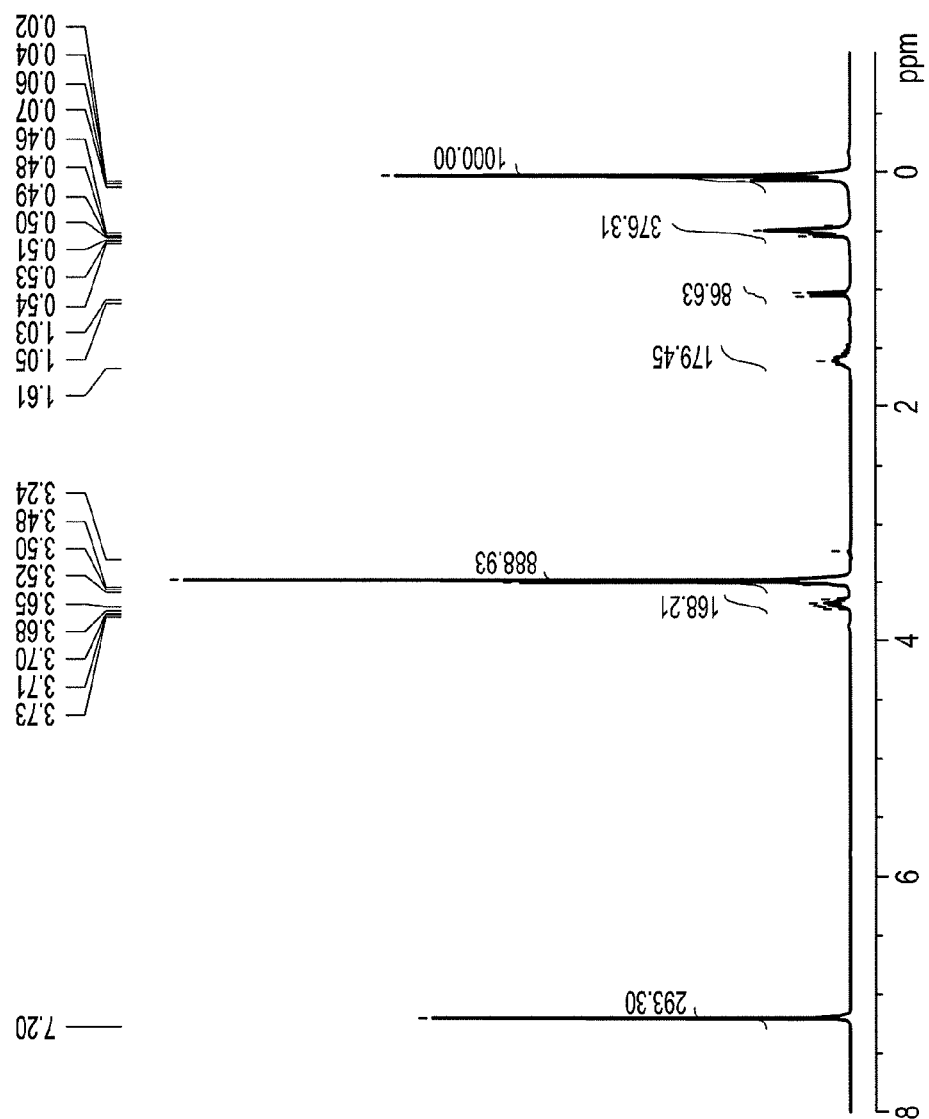
FIG. 12 is a $^1$H-NMR chart of Compound 6.

Compound 6 showed IR and $^1$H-NMR spectra as shown in FIGS. 11 and 12 with the following chemical shifts from TMS.

$^1$H-NMR spectra (δ, ppm)

| | |
|---|---|
| —SiCH$_3$, —CH— | 0.02~0.07 ppm |
| ≡SiCH$_2$CH$_2$Si≡ | 0.46~0.54 ppm |
| —CH— <br> \| <br> CH$_3$ | 1.03, 1.05 ppm |

Preparation of Surface Treatment Compositions

Surface treatment compositions 1 to 6 were prepared by dissolving each of the Compounds 1 to 6, respectively, in ethyl perfluorobutyl ether, HFE7200, ex Sumitomo 3M Co., to obtain 0.1 wt % solution. A sheet of an antireflection film (8 cm×15 cm×0.2 cm, ex Southwall Technologies Co.) was dipped in the composition for 10 seconds and pulled up at a speed of 150 mm/min. The sheet with its antireflective surface coated with the composition was left to stand for 24 hours in an environment of a temperature of 25° C. and a relative humidity of 40%. A cured coating layer was thus obtained.

Comparative Surface Treatment Compositions

Surface treatment compositions 7 and 8 were prepared in the same manner as described above by dissolving each of the following Compounds 7 and 8, respectively. A sheet of an antireflection film was treated with each of the compositions 7 and 8 in the same manner as described above.

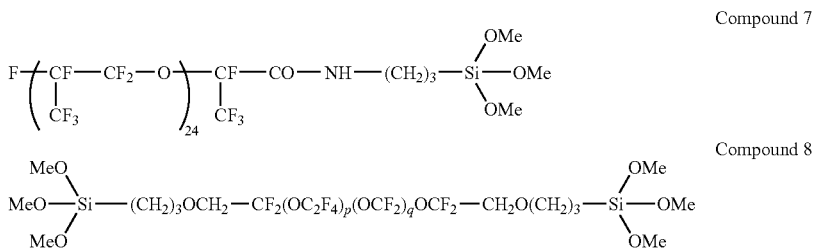

Compound 7

Compound 8

-continued

| | |
|---|---|
| —CH$_2$CH$_2$Si≡ | 1.61 ppm |
| —SiOCH$_3$ | 3.48~3.52 ppm |
| —CH$_2$OCH$_2$— | 3.65~3.73 ppm |

From the above data, Compound 6 was found to have the following structure.

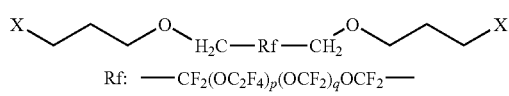

Rf: —CF$_2$(OC$_2$F$_4$)$_p$(OCF$_2$)$_q$OCF$_2$— wherein p/q was 0.9, p+q was 45 on average, and X is the following group.

wherein p/q is 0.9 and a Mw ranging from about 4000 to about 6000.

Evaluation of Cured Coating Layer

Cured coating layers obtained were evaluated according to the following methods. The results are as shown in Table 1.

Water Repellency and Oil Repellency

Using contact angle meter, Model A3, ex Kyowa Inter-FACE Science Co., Ltd., a water contact angle and an oleic acid receding contact angle of the cured coating layer were measured by sliding method.

Scrub Resistance

Using a rubbing tester, ex Shinto Scientific Co., Ltd., the cured coating was scrubbed under the following conditions:

Test environment: 25° C., relative humidity of 40%

Scrubbing material: The coating layers were scrubbed with a tip of the tester which was covered by eight sheets of nonwoven cloth (1.5 cm×1.5 cm) laid top on another and fixed by a rubber band.

Scrub distance (one way): 4 cm

Scrub speed: 500 cm/min
Load: 1 kg
Number of scrubbing: 1,000 times

On the scrubbed surface of the coating layer, a solvent ink was applied with a felt pen, Himackee, ex Zebra Co. Ltd. The surface of the coating was visually observed for repelled oil and evaluated according to the following criteria.

A: The ink was well repelled.
B: There was a part where the ink was not repelled.
C: The ink was not repelled at all.

TABLE 1

|  | Compound No. | Water contact angle, deg | Oleic acid receding contact angle, deg | Scrub Resistance |
|---|---|---|---|---|
| Examples | 1 | 113 | 66 | A |
|  | 2 | 113 | 56 | A |
|  | 3 | 102 | 61 | A |
|  | 4 | 109 | 67 | A |
|  | 5 | 109 | 65 | A |
|  | 6 | 110 | 67 | A |
| Comparative | 7 | 110 | 64 | C |
| Examples | 8 | 111 | 67 | C |

Compared with the antireflection films treated with the comparative compositions of 7 and 8, those treated with the compositions 1 to 6 had significantly larger scrub resistance and comparable water and oil resistance.

The present organopolysiloxane thus forms coating which firmly bonds to a substrate and is resistant to scrub, water and oil. The present organopolysiloxane and the surface treatment composition comprising the same are useful for surface treatment of various substrates.

The invention claimed is:

1. An organopolysiloxane represented by the following general formula (A), (B) or (C)

$$Si_n R^1{}_{2n+2} O_{n-1} \quad (A)$$

$$Si_n R^1{}_{2n} O_n \quad (B)$$

$$Si_n R^1{}_{2n+2} R^2{}_k O_{n-k-1} \quad (C)$$

wherein $R^1$ may be the same with or different from each other and is a hydrogen atom or a monovalent organic group, $R^2$ is an alkylene group having 2 to 6 carbon atoms, n is an integer of from 2 to 40 and k is an integer of 1 to 3, the formula (C) represents an organopolysiloxane containing a Si—$R^2$—Si bond, characterized in that at least two $R^1$'s are groups represented by the following formula (i):

$$\begin{array}{c} R^3{}_{3-a} \\ | \\ -C_y H_{2y} - Si - X_a \end{array} \quad (i)$$

wherein X is a hydrolyzable group, $R^3$ is an alkyl group having 1 to 4 carbon atoms or a phenyl group, y is an integer of from 1 to 5 and a is 2 or 3; and one SiOSi bond is replaced with a bond represented by the following formula (iii):

$$SiQR_f^2 QSi \quad (iii)$$

wherein $R_f^2$ is a divalent group containing a perfluoroether residue, and Q is a divalent organic group.

2. The organopolysiloxane according to claim 1, wherein n is an integer of from 2 to 10.

3. The organopolysiloxane according to claim 1, wherein the organopolysiloxane is represented by the formula (A) or (C), and has a ($SiO_2$) unit.

4. The organopolysiloxane according to claim 1, wherein $R^1$ is an alkyl group having 1 to 4 carbon atoms or a phenyl group.

5. The organopolysiloxane according to claim 1, wherein the perfluoroether residue contains 1 to 500 repeating units represented by the following general formula:

$$-C_g F_{2g} O-$$

wherein g is independently an integer of from 1 to 6.

6. The organopolysiloxane according to according to claim 1, wherein $R_f^2$ is selected from the groups represented by the following general formulas (5), (6), and (7):

$$-C_d F_{2d}(OCF_2 CF)_m O(C_r F_{2r} O)_s (CFCF_2 O)_n C_d F_{2d}- \quad (5)$$
$$\qquad\qquad | \qquad\qquad\qquad\qquad | $$
$$\qquad\qquad Y \qquad\qquad\qquad\qquad Y$$

wherein Y may be the same with or different from each other and is a fluorine atom or a $CF_3$ group, r is an integer of from 2 to 6, d is an integer of from 1 to 3, each of m and n is an integer of from 0 to 200 with m+n ranging from 2 to 200, s is an integer of from 0 to 6, and the repeating units may be bonded randomly;

$$-C_d F_{2d}(CF_2 CF_2 CF_2 O)_1 C_d F_{2d}- \quad (6)$$

wherein 1 is an integer of from 1 to 200 and d is an integer of from 1 to 3; and $$-C_d F_{2d}(OCF_2 CF)_m (OCF_2)_n OC_d F_{2d}- \quad (7)$$
$$\qquad\qquad | $$
$$\qquad\qquad Y$$

wherein Y is a fluorine atom or a $CF_3$ group, d is an integer of from 1 to 3, each of m and n is an integer of from 0 to 200 with m+n ranging from 2 to 200, and the repeating units may be bonded randomly.

7. The organopolysiloxane according to claim 1, wherein Q is a hydrocarbon group having 3 to 12 carbon atoms and may contain a bond selected from the group consisting of amide, ether, ester and vinyl bonds.

8. The organopolysiloxane according to claim 1, wherein X is selected from the group consisting of alkoxy groups, oxyalkoxy groups, acyloxy groups, alkenyloxy groups, and halogen atoms.

9. The organopolysiloxane according to claim 1, wherein X is selected from the group consisting of methoxy group, ethoxy group, isopropenoxy group and chlorine atom.

10. A surface treatment composition comprising, as an active ingredient, an organopolysiloxane represented by the following general formula (A), (B) or (C)

$$Si_n R^1{}_{2n+2} O_{n-1} \quad (A)$$

$$Si_n R^1{}_{2n} O_n \quad (B)$$

$$Si_n R^1{}_{2n+2} R^2{}_k O_{n-k-1} \quad (C)$$

wherein $R^1$ may be the same with or different from each other and is a hydrogen atom or a monovalent organic group, $R^2$ is an alkylene group having 2 to 6 carbon atoms, n is an integer of from 2 to 40 and k is an integer of 1 to 3, the formula (C) represents an organopolysiloxane containing a Si—R²—Si bond, characterized in that at least two R¹'s are groups represented by the following formula (i):

(i)

wherein X is a hydrolyzable group, R³ is an alkyl group having 1 to 4 carbon atoms or a phenyl group, y is an integer of from 1 to 5 and a is 2 or 3; and one SiOSi bond is replaced with a bond represented by the following formula (iii):

$$SiQR_f^2QSi \qquad (iii)$$

wherein $R_f^2$ is a divalent group containing a perfluoroether residue, and Q is a divalent organic group;

and/or a partial condensate of hydrolyzates of the organopolysiloxane.

11. The surface treatment composition according to claim 10, wherein n is an integer of from 2 to 10.

12. The surface treatment composition according to claim 10, wherein the organopolysiloxane is represented by the formula (A) or (C), and has a (SiO₂) unit.

13. The surface treatment composition according to claim 10, wherein R¹ is an alkyl group having 1 to 4 carbon atoms or a phenyl group.

14. The surface treatment composition according to claim 10, wherein the perfluoroether residue contains 1 to 500 repeating units represented by the following general formula:

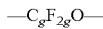

wherein g is independently an integer of from 1 to 6.

15. The surface treatment composition according to claim 10, wherein $R_f^2$ is selected from the groups represented by the following general formulas (5), (6), and (7):

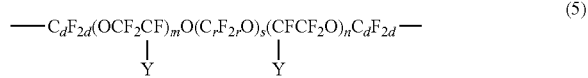

(5)

wherein Y may be the same with or different from each other and is a fluorine atom or a CF₃ group, r is an integer of from 2 to 6, d is an integer of from 1 to 3, each of m and n is an integer of from 0 to 200 with m+n ranging from 2 to 200, s is an integer of from 0 to 6, and the repeating units may be bonded randomly;

$$—C_dF_{2d}(CF_2CF_2CF_2O)_lC_dF_{2d}— \qquad (6)$$

wherein l is an integer of from 1 to 200 and d is an integer of from 1 to 3; and

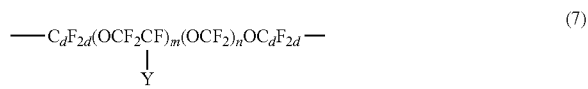

(7)

wherein Y is a fluorine atom or a CF₃ group, d is an integer of from 1 to 3, each of m and n is an integer of from 0 to 200 with m+n ranging from 2 to 200, and the repeating units may be bonded randomly.

16. The surface treatment composition according to claim 10, wherein Q is a hydrocarbon group having 3 to 12 carbon atoms and may contain a bond selected from the group consisting of amide, ether, ester and vinyl bonds.

17. The surface treatment composition according to claim 10, wherein X is selected from the group consisting of alkoxy groups, oxyalkoxy groups, acyloxy groups, alkenyloxy groups, and halogen atoms.

18. The surface treatment composition according to claim 10, wherein X is selected from the group consisting of methoxy group, ethoxy group, isopropenoxy group and chlorine atom.

19. A coated article treated with a cured composition formed from a surface treatment composition comprising, as an active ingredient, an organopolysiloxane represented by the following general formula (A), (B) or (C)

$$Si_nR^1_{2n+2}O_{n-1} \qquad (A)$$

$$Si_nR^1_{2n}O_n \qquad (B)$$

$$Si_nR^1_{2n+2}R^2_kO_{n-k-l} \qquad (C)$$

wherein R¹ may be the same with or different from each other and is a hydrogen atom or a monovalent organic group, R² is an alkylene group having 2 to 6 carbon atoms, n is an integer of from 2 to 40 and k is an integer of 1 to 3, the formula (C) represents an organopolysiloxane containing a Si—R²—Si bond, characterized in that at least two R¹'s are groups represented by the following formula (i):

(i)

wherein X is a hydrolyzable group, R³ is an alkyl group having 1 to 4 carbon atoms or a phenyl group, y is an integer of from 1 to 5 and a is 2 or 3; and one SiOSi bond is replaced with a bond represented by the following formula (iii):

$$SiQR_f^2QSi \qquad (iii)$$

wherein $R_f^2$ is a divalent group containing a perfluoroether residue, and Q is a divalent organic group;

and/or a partial condensate of hydrolyzates of the organopolysiloxane.

20. The coated article according to claim 19, wherein n is an integer of from 2 to 10.

21. The coated article according to claim 19, wherein the organopolysiloxane is represented by the formula (A) or (C), and has a (SiO₂) unit.

22. The coated article according to claim 19, wherein R¹ is an alkyl group having 1 to 4 carbon atoms or a phenyl group.

23. The coated article according to claim 19, wherein the perfluoroether residue contains 1 to 500 repeating units represented by the following general formula:

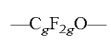

wherein g is independently an integer of from 1 to 6.

24. The coated article according to claim 19, wherein $R_f^2$ is selected from the groups represented by the following general formulas (5), (6), and (7):

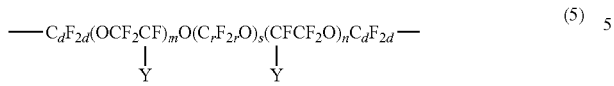
(5)

wherein Y may be the same with or different from each other and is a fluorine atom or a $CF_3$ group, r is an integer of from 2 to 6, d is an integer of from 1 to 3, each of m and n is an integer of from 0 to 200 with m+n ranging from 2 to 200, s is an integer of from 0 to 6, and the repeating units may be bonded randomly;

(6)

wherein l is an integer of from 1 to 200 and d is an integer of from 1 to 3; and

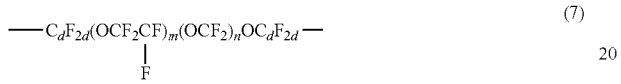
(7)

wherein Y is a fluorine atom or a $CF_3$ group, d is an integer of from 1 to 3, each of m and n is an integer of from 0 to 200 with m+n ranging from 2 to 200, and the repeating units may be bonded randomly.

25. The coated article according to claim 19, wherein Q is a hydrocarbon group having 3 to 12 carbon atoms and may contain a bond selected from the group consisting of amide, ether, ester and vinyl bonds.

26. The coated article according to claim 19, wherein X is selected from the group consisting of alkoxy groups, oxyalkoxy groups, acyloxy groups, alkenyloxy groups, and halogen atoms.

27. The coated article according to claim 19, wherein X is selected from the group consisting of methoxy group, ethoxy group, isopropenoxy group and chlorine atom.

* * * * *